United States Patent [19]
Davis et al.

[11] Patent Number: 6,114,333
[45] Date of Patent: Sep. 5, 2000

[54] 2-PYRIMIDINEAMINE DERIVATIVES AND PROCESSES FOR THEIR PREPARATION

[75] Inventors: Peter David Davis, Aston Rowant; David Festus Charles Moffat, Maidenhead; Mark James Batchelor, Cumnor Hill; Martin Clive Hutchings, Wokingham; David Mark Parry, Twyford, all of United Kingdom

[73] Assignee: Celltech Therapeutics Ltd., United Kingdom

[21] Appl. No.: 08/958,419

[22] Filed: Oct. 27, 1997

[30] Foreign Application Priority Data

Oct. 28, 1996 [GB] United Kingdom ............. 9622363

[51] Int. Cl.$^7$ .............. A61K 31/505; A61K 31/535; C07D 401/14; C07D 405/14
[52] U.S. Cl. ............. 514/252; 540/575; 544/60; 544/122; 544/295; 544/331; 514/210; 514/218; 514/227.8; 514/235.8; 514/253; 514/275
[58] Field of Search ............... 540/575; 544/60, 544/122, 295, 331; 514/210, 218, 227.8, 235.8, 252, 253, 275

[56] References Cited

U.S. PATENT DOCUMENTS

| | | | |
|---|---|---|---|
| 4,012,495 | 3/1977 | Schmiechen et al. | 514/424 |
| 4,015,017 | 3/1977 | Gazave | 514/687 |
| 4,153,713 | 5/1979 | Huth et al. | 514/423 |
| 4,193,926 | 3/1980 | Schmiechen et al. | 548/517 |
| 4,303,649 | 12/1981 | Jones | 514/8 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,159,078 | 10/1992 | Rempfler et al. | 544/330 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,521,185 | 5/1996 | Zimmermann | 514/252 |
| 5,550,137 | 8/1996 | Beeley et al. | 514/354 |
| 5,580,888 | 12/1996 | Warrellow et al. | 514/332 |
| 5,593,997 | 1/1997 | Dow et al. | 514/258 |
| 5,608,070 | 3/1997 | Alexander et al. | 546/270 |
| 5,622,977 | 4/1997 | Warrellow et al. | 514/336 |
| 5,693,659 | 12/1997 | Head et al. | 514/357 |
| 5,728,708 | 3/1998 | Zimmerman | 514/275 |
| 5,739,144 | 4/1998 | Warrellow et al. | 514/277 |
| 5,753,663 | 5/1998 | Flippin et al. | 514/257 |

FOREIGN PATENT DOCUMENTS 0 233 461 A2  8/1987  European Pat. Off. .
0 295 210 A1  12/1988 European Pat. Off. .

(List continued on next page.)

OTHER PUBLICATIONS

Chatterjee, A. et al., "Total Synthesis of Ring–C Aromatic 18–Nor Steroid", *Tetrahedron*, 1980, 36, 2513–2519.

Clayton, S.E. et al., "Direct Aromatic tert–Butylation during the Synthesis of Thiochroman–4–ones", *Tetrahedron*, 1993, 49(4), 939–946.

Collins, R.F. et al., "The Chemotherapy of Schistosomiasis. Part IV. Some Ethers of 4–Amino–2–methoxyphenol", *J. Chem. Soc.*, 1961, 1863–1879.

Degani, I. et al., "Cationi etero–aromatici Nota VI—Sintesi di alcuni derivati del perclorato di tiacromilio", *Boll. Sci. Fac. Chim. Ind. Bologna*, 1966, 24(2–3), 75–91 (English Summary Only).

Geissler et al., "Biochemical and Biological Activity of a Novel Class of Tyrosine Protein Kinase Inhibitors", *J. Biol. Chem.*, 1990, 265(36), 22255–22261.

Griffin, R.W. et al., "1–Methyl–7–halo–2–naphthalenecarboxylic Acid Derivatives", *J. Organic Chem.*, 1964, 29(8), 2109–2116.

Gupta, A.S. et al., "Friedel–Crafts Condensation of Ethyl Allylmalonate with Anisole", *Tetrahedron*, 1967, 23, 2481–2490.

(List continued on next page.)

*Primary Examiner*—Mukund J. Shah
*Assistant Examiner*—Ann Kessinger
*Attorney, Agent, or Firm*—Woodcock Washburn Kurtz Mackiewicz & Norris LLP

[57] ABSTRACT

Compounds of general formula (1)

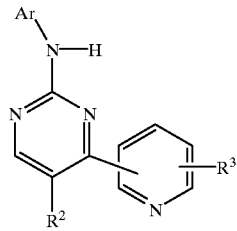

(1)

are described wherein:

Ar is an optionally substituted aromatic group;

$R^2$ is a hydrogen or halogen atom or a group $-X^1-R^{2a}$ where $X^1$ is a direct bond or a linker atom or group, and $R^{2a}$ is an optionally substituted straight or branched chain alkyl, alkenyl or alkynyl group;

$R^3$ is an optionally substituted heterocycloalkyl group; and the salts, solvates, hydrates and N-oxides thereof.

The compounds are selective protein tyrosine kinase inhibitors, particularly the kinases ZAP-70 and syk and are of use in the prophylaxis and treatment of immune or allergic diseases and diseases involving inappropriate platelet activation.

6 Claims, No Drawings

FOREIGN PATENT DOCUMENTS

| | | |
|---|---|---|
| 0 337 943 A2 | 10/1989 | European Pat. Off. . |
| 0 393 500 A1 | 10/1990 | European Pat. Off. . |
| 0 490 823 A1 | 6/1991 | European Pat. Off. . |
| 0 470 805 A1 | 2/1992 | European Pat. Off. . |
| 0 497 564 A1 | 8/1992 | European Pat. Off. . |
| 0 511 865 A1 | 11/1992 | European Pat. Off. . |
| 0 537 742 A2 | 4/1993 | European Pat. Off. . |
| 0 564 409 A1 | 10/1993 | European Pat. Off. . |
| 2 545 356 A1 | 11/1984 | France . |
| 250 1443 | 7/1975 | Germany . |
| 3-77872 | 4/1991 | Japan . |
| 3-77923 | 4/1991 | Japan . |
| 1588639 | 4/1981 | United Kingdom . |
| WO 87/06576 | 11/1987 | WIPO . |
| WO 91/15451 | 10/1991 | WIPO . |
| WO 91/16892 | 11/1991 | WIPO . |
| WO 92/00968 | 1/1992 | WIPO . |
| WO 92/06085 | 4/1992 | WIPO . |
| WO 92/06963 | 4/1992 | WIPO . |
| WO 92/07567 | 5/1992 | WIPO . |
| WO 92/12961 | 8/1992 | WIPO . |
| WO 92/19594 | 11/1992 | WIPO . |
| WO 92/19602 | 11/1992 | WIPO . |
| WO 93/10118 | 5/1993 | WIPO . |
| WO 93/19748 | 10/1993 | WIPO . |
| WO 94/02465 | 2/1994 | WIPO . |
| WO 94/10118 | 5/1994 | WIPO . |
| WO 94/12461 | 6/1994 | WIPO . |
| WO 94/13661 | 6/1994 | WIPO . |
| WO 94/14742 | 7/1994 | WIPO . |
| WO 94/20446 | 9/1994 | WIPO . |
| WO 94/20455 | 9/1994 | WIPO . |
| WO 95/04046 | 2/1995 | WIPO . |
| 95/09853 | 4/1995 | WIPO . |
| WO 95/09847 | 4/1995 | WIPO . |
| WO 95/09851 | 4/1995 | WIPO . |
| WO 95/09852 | 4/1995 | WIPO . |
| WO 95/09853 | 4/1995 | WIPO . |
| WO 95/17386 | 6/1995 | WIPO . |
| WO 95/31451 | 11/1995 | WIPO . |
| WO 95/33727 | 12/1995 | WIPO . |
| WO 95/35281 | 12/1995 | WIPO . |
| WO 95/35283 | 12/1995 | WIPO . |
| WO 96/14843 | 5/1996 | WIPO . |
| WO 97/09297 | 3/1997 | WIPO . |

OTHER PUBLICATIONS

Hart et al., "Alkylation of Phenol with a Homoallylic Halide", *J. Am. Chem. Soc.,* 1963, 85, 3269–3273.

Johnson et al., "Identification of Retinoic Acid Receptor β Subtype Specific Agonists", *J. Med. Chem.,* 1996, 39(26), 5027–5030.

Lehmann, J. et al., "Lactones; XIII. Grignard Reaction Followed by Phase–Transfer Oxidation: A Convenient Synthesis of γ,γ–Distributed γ–Butyrolactones from γ–Butyrolactone", *Synthesis,* 1987, 1064–1067 (English abstract only).

Meyers, A.I. et al., "The Synthesis of 2–Pyridones from Cyclic Cyano Ketones. A New Aromatization Procedure for Dihydro–2–pyridones", *J. Org. Chem.,* 1964, 29, 1435–1438.

Kefalas, P. et al., "Signalling by the $p60^{c-src}$ Family of Protein–Tyrosine Kinases", *Int. J. Biochem. Cell Biol.,* 1995, 27(6), 551–563.

Chemical Abstracts, Registry No. 2732–15–2, prior to 1967, 1 page.

Chemical Abstracts, Registry No. 4593–13–9, prior to 1967, 1 page.

Bortolus et al., "cis–trans Isomerization of azastilbenes photosensitized by biacetyl", *Mol. Photochem.,* 1970 2(4), 311–321, CAPLUS accession No. 1971–434722, 2 pages.

Kaiser et al., "Selective metalations of methylated pyridines and quinolines", *J. Org. Chem.,* 1973, 38(1), 71–75, CAPLUS accession No. 1973–71853, 2 pages.

Pickett, W.C. et al., "Modulation of Eicosanoid Biosynthesis by Novel Pyridinylpyrimidines", *Ann. N.Y. Acad. Sci.,* 1994, 744, 299–305.

Spada, A.P. et al., "Small Molecule Inhibitors of Tyrosine Kinase Activity", *Exp. Opin. Ther. Patents,* 1995, 5(8), 805–817.

Yamaguchi, H., "Guanidinobenzene derivatives as anticoagulants", *Chem. Absts.,* 1989, 110, 655 (Abstract No. 94706z).

Zimmermann, J. et al., "Phenylamino–Pyrimidine (PAP) Derivatives: A New Class of Potent and Selective Inhibitors of Protein Kinase C (PKC)", *Arch. Pharm.,* 1996, 329(7), 371–376.

Zimmermann, J. et al, "Phenylamino–Pyrimidine (PAP)— Derivatives: A New Class of Potent and Highly Selective PDGF–Receptor Autophosphorylation Inhibitors", *Bioorg. Med. Chem. Lett.,* 1996, 6(11), 1221–1226.

Zimmermann, J. et al., "Potent and Selective Inhibitors of the ABL–Kinase Phenylamino–Pyrimidine (PAP) Derivatives", *Bioorg. Med. Chem. Lett.,* 1997, 7(2), 187–192.

Ashton, "Selective Type IV Phosphodiesterase Inhibitors as Antiasthmatic Agents. The Syntheses and Biological Activities of 3–(Cyclopentyloxy)–4–methyoxybenzamides and Analogues", *J. Med. Chem.,* 1994, 37, 1696–1703.

Beavo & Reifsnyder, "Primary Sequence of Cyclic Nucleotide Phosphodiesterase Isozymes and the Design of Selective Inhibitors" *TIPS,* 1990, 11, 150–155.

Buu–Hoi, N.P. et al., "Bromination of Some 1,2,2–Triarylethylenes" *J. of Organic Chemistry,* 1958, 1261–1263.

Buu–Hoi et al., "New Method for the Synthesis of ω,ω–Diarylacetophenones Aminated in the Aromatic Nucleus. Plynitration of Triarylethylenes", *Chem. Abstr.,* 1964, 61(13), 16006h.

Chan, A.C. et al., "The Role of Protein Tyrosine Kinases and Protein Tyrosine Phosphatases in T Cell Antigen Receptor Signal Transduction", *Annu. Rev. Immunol.,* 1994, 12, 555–592.

Chemical Abstracts, "Hypoglycemic Pharmaceuticals Containing Manzammide Derivatives", *Chem. Abstr.,* 1983, 99(6), No. 43558Z.

Chemical Abstracts. Registry Handbook—Number Section. Printed Issues Columbus US *compounds with registry Nos. 95992–21–5; 95971–60–1; 90053–37–5; 82668–18–6; 80395–25–1; 49610–49–3.

Daves, G.D. et al., "Pyrimidines. XIII. 2– and 6– Substituted 4–Pyrimidinecarboxylic Acids", *J. Of Hev. Chem.,* 1964, 1, 130–133.

Dietl, F. et al., "Chinone von Benzo–und Dibenzokroneneth-ern", *Synthesis,* 1985, 626–631.

Dent et al., "Inhibition of eosinophil cyclic nucleotide PDE activity and opsonised zymosan–stimulated respiratory burst by 'type IV'–selective PDE inhibitors", *Br. J. Pharmacol.,* 1991, 103, 1339–1346.

El–Wakil et al., "Study of the proton magnetic resonance of methoxytamoxifen towards ortho–substitiution", *Chem. Abstr.,* 1992, 116, 255248t.

Geissler, J.F. et al., "Thiazolidine–Diones. Biochemical and Biological Activity of a Novel Class of Tyrosine Protein Kinase Inhibitors", *J. Of Biol. Chem.*, 1990, 265(36), 22255–22261.

Grammaticakis, "Contribution A L'Etude de L'Absortion Dans L'Ultraviolet Moyen Et Le Visible Des N–Aroyl–Arylamines. IV. 2,3–,3,4– et 2,4–, dimethoxybenzoylarylamines", *Bulletin DeLa Societa Chemique De France*, 1965, 848–858.

Green and Wuts, "Protective Group in Organic Synthesis", John Wiley & Sons, New York, 1991.

Hanks, S.K. et al., "The eukaryotic protein kinase superfamily: kinase (catalytic) domain structure and classification", *FASEB J.*, 1995, 9, 576–596.

Heaslip et al., "Phosphodiesterase–IV Inhibition, Respiratory Muscle Relaxation and Bronchodilation by WAY–PDA–641", *J. Pharm. Exper. Ther.*, 1993, 268(2), 888–896.

Hirose et al., "Styrene Derivatives and Electrophotpgraphic Photoreceptor Containing Them", *Chem. Abstr.*, 1993, 118, 136183z.

Ishikura, M. et al., "An Efficient Synthesis of 3–Heteroarylpyridines via Diethyl–(3–pyridyl)–borane" *Synthesis*, 1984, 936–938.

Iwashita, S. et al., "Signal Transduction System for Growth Factor Receptors Associated with Tyrosine Kinase Activity: Epidermal Growth Factor Receptor Singalling and Its Regulation", *Cellular Signalling*, 1992, 4(2), 123–132.

Karlsson et al., "T–Lymphocyte and Inflammatory Cell Research in Asthma", Joller, G. et al. (eds.), Academic Press, 1993, 323–347.

Lisle, H. et al., "IL–2–Induced Eosinophilia in the Rat Pleural Cavity: The Effect of Dexamethasone and Indomethacin", *Br. J. Pharmacol.* 1993, 108, 230.

Livi et al., "Cloning and Expression of cDNA for a Human Low-$K_m$3 Rolipram–sensitive Cyclic AMP Phosphodiesterase", *Molecular and Cellular Biol.* 1990, 10(6), 2678–2686.

Manhas et al., "heterocyclic Compounds XII. Quinazoline Derivatives as Potential Antifertility Agents(1)" *J. Heterocyclic Chem.*, 1979, 16, 711–715.

Mathison et al., "Synthesis and Hypotensive Properties of Tetrahydroixoquinolines", *J. Med. Chem.*, 1973, 16(4), 332–336.

Meyers, A.J. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 1974, 39(18), 2787–2793.

Mezheritskaya, "Synthesis and properties of carboxonium het=erocyclic systems. VII. Synthesis and properties of 2–benzyl–substituted 1,3–dioxolanium salts", *Chem. Abstr.*, 1980, 93, 95160j, 635.

Mitsunobu, O., "The Use of Diethyl Azodicarboxylate and Triphenylphosphine in Synthesis and Transformation of Natural Products" *Synthesis*, 1981, 1–28.

Miyaura, N. et al., "The Palladium–Catalyzed Cross–Coupling Reaction of Phenylboronic Acid with Haloarenes in the Presence of Bases", *Synth. Comm.*, 1981, 11, 513–519.

Newton, A.C., "Protein Kinase C: Structure, Function, Regulation", *J. Biol. Chem.*, 1995, 270(48), 28495–28498.

Nicholson et al., "Differential Modulation of Tissue Function and Therapeutic Potential of Selective Inhibitors of Cyclic Nucleotide Phosphodiesterase Isoenzymes" *TIPS*, 1991, 12, 19–27.

O'Connor et al., "Voltammetry and Controlled Potential Oxidation of 3,4–dimethoxypropenylbenzene at a rotating platinum electrode in unbuffered acetonitrile and in acetonitrile–pyridine solution" *Chem. Abstr.*, 1964, 60(8) #10203.4.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Pines, J., "Cyclins and cyclin–dependent kinases: take your partners", *TIBS*, 1993, 18, 195–197.

Plé, N. et al., "Metalation of Diazines. XI. Directed Ortho–Lithiation of Fluoropyrimidines and Application to Synthesis of an Azacarboline", *J. Heterocyclic Chem.*, 1994, 31, 1311–1315.

Porter et al., "Preparation of 6–phenyl–3–(5–tetrazolyl)pyridin–=2(H)–one Derivatives as Cyclic AMP–dependent Protein Kinase Agonists" *Chem. Abstr.*, 1992, 117(9), 90296n.

Ramalingam, Deshmukh and Sattur, "Synthesis and Pharmacology of 2,5–Disubstituted 1,3,4–Zxadiazoles" *J. Indian Chem. Soc.*, 1981, 58(3), 269–271.

Reddy et al., "Inhibition of Breast Cancer Cell Growth in Vitro by a Tyrosine Kinase Inhibitor" *Cancer Research*, 1992, 52, 3636–3641.

Sakakibara, K. et al., "Preparation of N–pyridyl–4–(benzyloxy)benzamides as Cardiotonics", *Chem. Abstr.*, 1988, 108, No. 131583p.

Sánchez, H.I. et al., "Formal Total Syntehsis of β–Pipitzol", *Tetrahedron*, 1985, 41(12), 2355–2359.

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" *J. Med. Chem.*, 1986, 29, 1355–1362.

Seitz et al., "Fluorotamoxifen. A Caveat on the Generality of Electrophilic Destannylation" *Chem. Abstr.*, 1989, 111, 57133k.

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls", *Tetrahedron Lett.*, 1987, 28(43), 5093–5096.

Shioiri et al., "New Methods and Reagents in Organic Synthesis. 3. Diethyl Phosphorocyanidate: A New Reagent for C–Acylation", *J. Org. Chem.*, 1978, 43, 3631–3632.

Takeuchi, I. et al., "On the Antimocrobial Activity and Syntheses of Carbanilide and Salicylanilide Derivatives", *Chem. Abstr.*, 1983, 98, No. 125577y.

Thompson, W.J. and Gaudino, J., "A General Synthesis of 5–Arylnicotinates" *J. Org. Chem.*, 1984, 49, 5237–5243.

Tominaga et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo[3,4–d]pyrimidines, and 5–Aza [2.2.3]cyclazines", *J. Het. Chem.*, 1990, 27, 647–660.

Trost and Fleming (eds.), Comprehensive Organic Synthesis, Pergamon Press, New York, 1991, 3, 531–541.

Tsutsumi, K. et al., "Preparation of (Dialkoxyphosphinoyl-methyl) benzamides as Antihyperlipidemics", *Chem. Abstr.*, 1990, 113, No. 6599a.

Vidal et al., "Electrophilic Amination: Preparation and Use of N–Boc–3–(4–cyanophenyl) oxaziridine, a New Regent That Transfers a N–Boc Group to N– and C–Nucleophiles", *J. Org. Chem.*, 1993, 58, 4791–4793.

Yeadon et al., "Mechanisms Contributing to Ozone–Induced Bronchial Hyperreactivity in Guinea Pigs", *Pulmonary Pharm.*, 1992, 5, 39–50.

Yoneda et al., "The Antiproliferative Effects of Tyrosine Kinase Inhibitors Tyrphostins on a Human Squamous Cell Carcinoma in Vitro and in Nude Mice" *Cancer Research*, 1991, 51, 4430–4435.

2-PYRIMIDINEAMINE DERIVATIVES AND PROCESSES FOR THEIR PREPARATION

This invention relates to 2-pyrimidineamine derivatives, to processes for their preparation, to pharmaceutical compositions containing them, and to their use in medicine.

Protein kinases participate in the signalling events which control the activation, growth and differentiation of cells in response to extracellular mediators and to changes in the environment. In general, these kinases fall into two groups; those which preferentially phosphorylate serine and/or threonine residues and those which preferentially phosphorylate tyrosine residues [Hanks, S K, Hunter T, FASEB. J. 9, 576–596 (1995)]. The serine/threonine kinases include for example, protein kinase C isoforms [Newton A C, J. Biol. Chem. 270, 28495–28498 (1995)] and a group of cyclin-dependent kinases such as cdc2 [Pines J, Trends in Biochemical Sciences 18, 195–197 (1995)]. The tyrosine kinases include membrane-spanning growth factor receptors such as the epidermal growth factor receptor [Iwashita S and Kobayashi M. Cellular Signalling 4, 123–132 (1992)], and cytosolic non-receptor kinases such as p56$^{lck}$ p59$^{fyn}$ ZAP-70 and csk kinases [Chan C et al Ann. Rev. Immunol. 12, 555–592 (1994)].

Inappropriately high protein kinase activity has been implicated in many diseases resulting from abnormal cellular function. This might arise either directly or indirectly, for example by failure of the proper control mechanisms for the kinase, related for example to mutation, overexpression or inappropriate activation of the enzyme; or by over- or underproduction of cytokines or growth factors also participating in the transduction of signal upstream or downstream of the kinase. In all of these instances, selective inhibition of the action of the kinase might be expected to have a beneficial effect.

We have now found a series of 2-pyrimidineamine derivatives which are potent and selective inhibitors of the protein tyrosine kinases ZAP-70 and syk. The ZAP-70 kinase is involved in the transduction of signals from the T-cell receptor and thus in the activation of T-cells during the immune response. The closely related kinase syk is involved in signalling from the B-cell receptor and thus in the activation of B-cells during the immune response [van Oers N S, Weiss A, Seminars in Immunology, 7, 227–236, (1995)] and is also involved in signalling from the Fc epsilon Rl, the high-affinity IgE receptor present on mast cells [Zhang J, et al, J. Exp. Med. 184, 71–79 (1996)] and in the survival of eosinophils mediated by IL5 and GM-CSF [Yousefi S, et al J. Exp. Med. 183, 1407–1414, (1996)]. Syk is further involved in the activation of platelets stimulated via the low-affinity IgG receptor (Fc gamma-RIIA) or stimulated by collagen [Yanaga F, et al, Biochem. J. 311, (Pt. 2) 471–478, (1995)].

The compounds of the invention are thus of use in the prophylaxis and treatment of immune diseases (including autoimmune diseases and transplant rejection), allergic diseases involving mast cells or eosinophils, and diseases involving inappropriate platelet activation.

Thus, according to one aspect of the invention, we provide a compound of formula (1):

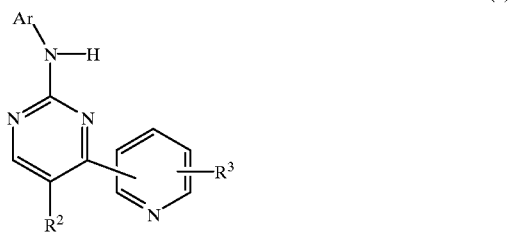

wherein Ar is an optionally substituted aromatic group;
$R^2$ is a hydrogen or halogen atom or a group —$X^1$—$R^{2a}$ where $X^1$ is a direct bond or a linker atom or group, and $R^{2a}$ is an optionally substituted straight or branched chain alkyl, alkenyl or alkynyl group;
$R^3$ is an optionally substituted heterocycloalkyl group; and the salts, solvates, hydrates and N-oxides thereof.

It will be appreciated that in the compounds of formula (1) the pyrimidine and $R^3$ groups may be attached to any ring carbon atom of the pyridyl group, provided always that they are not both attached to the same carbon atom.

The group $R^2$ in compounds according to the invention may be for example a hydrogen or halogen atom such as a fluorine, chlorine, bromine or iodine atom, or a group —$X^1$—$R^{2a}$ where $X^1$ is a direct bond or linker atom or group, and $R^{2a}$ is an optionally substituted straight or branched chain alkyl, alkenyl or alkynyl group.

Linker atoms represented by $X^1$ when present in compounds of formula (1) include —O— or —S— atoms. When $X^1$ is a linker group it may be for example a —C(O)—, —C(S)—, —S(O)—, —S(O)$_2$—, —N($R^7$)— [where $R^7$ is a hydrogen atom or a $C_{1-6}$ alkyl, e.g. methyl or ethyl, group], —CON($R^7$)—, —OC(O)N($R^7$)—, —CSN(R7)—, —N($R^7$)CO—, —N($R^7$)C(O)O—, —N($R^7$)CS—, —SON($R^7$), —SO$_2$N($R^7$), —N($R^7$)SO$_2$—, —N($R^7$)CON($R^7$)—, —N($R^7$)CSN($R^7$)—, —N($R^7$)SON($R^7$)— or —N($R^7$)SO$_2$N($R^7$) group.

When $R^{2a}$ is present in compounds of the invention it may be for example an optionally substituted straight or branched chain $C_{1-6}$ alky, e.g. $C_{1-3}$ alkyl, $C_{2-6}$ alkenyl e.g. $C_{2-4}$ alkenyl or $C_{2-6}$ alkynyl e.g. $C_{2-4}$ alkynyl group. Particular examples of such groups include optionally substituted —CH$_3$, —CH$_2$CH$_3$, —(CH$_2$)$_2$CH$_3$, —CH(CH$_3$)$_2$, —(CH$_2$)$_3$CH$_3$, —CH(CH$_3$)CH$_2$CH$_3$, —CH$_2$CH(CH$_3$)$_2$, —C(CH$_3$)$_3$, —(CH$_2$)$_4$CH$_3$, —(CH$_2$)$_5$CH$_3$, —CHCH$_2$, —CHCHCH$_3$, —CH$_2$CHCH$_2$, —CHCHCH$_2$CH$_3$, —CH$_2$CHCHCH$_3$, —(CH$_2$)$_2$CHCH$_2$, —CCH, —CCCH$_3$, —CH$_2$CCH, —CCCH$_2$CH$_3$, —CH$_2$CCCH$_3$ or —(CH$_2$)$_2$CCH groups. The optional substituents which may be present on these groups include one, two, three or more substituents selected from halogen atoms, e.g. fluorine, chlorine, bromine or iodine atoms, or hydroxyl, $C_{1-6}$ alkoxy, e.g. methoxy or ethoxy, thiol, $C_{1-6}$ alkylthio, e.g. methylthio or ethylthio, amino $C_{1-6}$ alkylamino, e.g. methylamino or ethylamino, or $C_{1-6}$ dialkylamino, e.g. dimethylamino or diethylamino groups.

$R^3$ in compounds of formula (1) may be for example an optionally substituted heteroC$_{3-7}$cycloalkyl group containing one or two oxygen, or sulphur atoms or nitrogen containing groups. The heterocycloalkyl group may be attached to the remainder of the molecule of formula (1) through any of its carbon or, where present, nitrogen atoms as appropriate.

Where desired, any available nitrogen or carbon atom in $R^3$ may be substituted by a group $R^4$ where $R^4$ is an optionally substituted straight or branched chain $C_{1-6}$ alkyl, $C_{1-6}$ alkoxy, hydroxyl (—OH), amino (—NH$_2$), —NHR$^{1a}$ [where R$^{1a}$ is an optionally substituted straight or branched chain $C_{1-6}$ alkyl group], —NR$^{1a}$R$^{1b}$ [where R$^{1b}$ is as defined for R$^{1a}$ and may be the same as or different to R$^{1a}$], carboxyl (—CO$_2$H), esterified carboxyl (—CO$_2$Alk$^1$, where Alk$^1$ is as defined below in connection with the group R$^5$), —COR$^{1a}$, carboxamido (—CONH$_2$), thiocarboxamido (—CSNH$_2$), —CONHR$^{1a}$, —CONR$^{1a}$R$^{1b}$, —CSNHR$^{1a}$, —CSNR$^{1a}$R$^{1b}$, —SO$_2$R$^{1a}$, —SO$_2$NH$_2$, —SO$_2$NHR$^{1a}$, —SO$_2$NR$^{1a}$R$^{1b}$, imido, —SC(NH)NH$_2$, —NHC(NH)NH$_2$, —NHC(NH)R$^{1a}$ or an optionally substituted aromatic group. Additionally, any available carbon atom in the heterocycloalkyl group represented by R$^3$ may be linked to an oxygen or sulphur atom to form a —C(O)— or —C(S)— group.

The heterocycloalkyl group R$^3$ may contain one, two, three or more R$^4$ substituents, the upper limit depending on the size of the ring and number of available carbon and/or nitrogen atoms.

When the substituent R$^4$ is an optionally substituted alkyl or alkoxy group it may be for example an optionally substituted methyl, ethyl, prop-1-yl, prop-2-yl, methoxy or ethoxy group.

The groups R$^{1a}$ and R$^{1b}$ when present in the substituent R$^4$ may be for example optionally substituted $C_{1-3}$ alkyl groups such as optionally substituted methyl or ethyl groups.

Optional substituents which may be present on alkyl or alkoxy groups represented by R$^4$, or in R$^{1a}$ and/or R$^{1b}$ groups, include one or two substituents selected from $C_{1-6}$ alkoxy, —OH, —NH$_2$, —NHR$^{1a}$, —NR$^{1a}$R$^{1b}$, —CO$_2$H, —CO$_2$Alk$^1$, —COR$^{1a}$, —CONH$_2$, —CSNH$_2$, —CONHR$^{1a}$, —CONR$^{1a}$R$^{1b}$, —CSNHR$^{1a}$, —CSNR$^{1a}$R$^{1b}$, —SO$_2$R$^{1a}$, —SO$_2$NH$_2$, —SO$_2$NHR$^{1a}$, —SO$_2$NR$^{1a}$R$^{1b}$, imido, —SC(NH)NH$_2$, —NHC(NH)NH$_2$, —NHC(NH)R$^{1a}$ or optionally substituted aromatic groups.

Optionally substituted aromatic groups represented by the substituent R$^4$ or present as an optional substituent on a group R$^4$, R$^{1a}$ or R$^{1b}$ include optionally substituted Ar$^1$ groups where Ar$^1$ is as defined herein for the group Ar. The optional substituents which may be present on the group Ar$^1$ include those —R$^5$ or —Alk(R$^5$)$_m$ substituents described below in relation to the group Ar.

Particular examples of R$^3$ groups include optionally substituted azetidinyl, pyrrolidinyl, piperidinyl, piperazinyl, homopiperazinyl, morpholinyl or thiomorpholinyl groups. As explained above, these particular heterocycloalkyl groups may be attached to the remainder of the compound of the invention through any of their available ring carbon or nitrogen atoms.

Particular R$^4$ substituents which may be present on R$^3$ heterocycloalkyl groups include for example —CH$_3$, —CH$_2$CH$_3$, —(CH$_2$)$_2$CH$_3$, —CH(CH$_3$)$_2$, —OH, —OCH$_3$, —OCH$_2$CH$_3$, —O(CH$_2$)$_2$NH$_2$, —O(CH$_2$)$_2$NHCH$_3$, —O(CH$_2$)N(CH$_3$)$_2$, —CH$_2$OH, —(CH$_2$)$_2$OH, —(CH$_2$)$_3$OH, —CH$_2$NH$_2$, —CH$_2$NHCH$_3$, —CH$_2$N(CH$_3$)$_2$, —(CH$_2$)$_2$NH$_2$, —(CH$_2$)$_2$NHCH$_3$, —(CH$_2$)$_2$N(CH$_3$)$_2$, —NH$_2$, —NHCH$_3$, —N(CH$_3$)$_2$, —SO$_2$NH$_2$, —SO$_2$NHCH$_3$, —SO$_2$N(CH$_3$)$_2$, —(CH$_2$)$_3$-phthalimido, —Ar$^1$ or —CH$_2$Ar$^1$ groups where in each instance Ar$^1$ is an optionally substituted phenyl group.

Aromatic groups represented by Ar in compounds of formula (1) include for example optionally substituted monocyclic or bicyclic fused ring $C_{6-12}$ aromatic groups, such as optionally substituted phenyl, 1- or 2-naphthyl, indanyl or indenyl groups.

Optional substituents which may be present on the aromatic group Ar include one, two, three or more substituents each represented by the atom or group R$^5$ or —Alk(R$^5$)$_m$ where R$^5$ is a halogen atom, or an amino (—NH$_2$), substituted amino, nitro, cyano, hydroxyl (—OH), substituted hydroxyl, formyl, carboxyl (—CO$_2$H), esterified carboxyl, thiol (—SH), substituted thiol, —COR$^6$ [where R$^6$ is a —Alk(R$^5$)$_m$, aryl or heteroaryl group], —CSR$^6$, —SO$_3$H, —SO$_2$R$^6$, —SO$_2$NH$_2$, —SO$_2$NHR$^6$, SO$_2$N[R$^6$]$_2$, —CONH$_2$, —CSNH$_2$, —CONHR$^6$, —CSNHR$^6$, —CON[R$^6$]$_2$, —CSN[R$^6$]$_2$, —NHSO$_2$H, —NHSO$_2$R$^6$, —N[SO$_2$R$^6$]$_2$, —NHSO$_2$NH$_2$, —NHSO$_2$NHR$^6$, —NHSO$_2$N[R$^6$]$_2$, —NHCOR$^6$, —NHCONH$_2$, —NHCONHR$^6$, —NHCON[R$^6$]$_2$, —NHCSR$^6$, —NHC(O)OR$^6$, cycloalkyl, heterocycloalkyl, aryl or heteroaryl group; Alk is a straight or branched $C_{1-6}$ alkylene, $C_{2-6}$ alkenylene or $C_{2-6}$ alkynylene chain, optionally interrupted by one, two or three —O— or —S— atoms or groups selected from S—(O)—, —S(O)$_2$— or —N(R$^6$)— [where R$^6$ is a hydrogen atom or a straight or branched chain $C_{1-6}$ alkyl group]; and m is zero or an integer 1, 2 or 3.

When in the group —Alk(R$^5$)$_m$ m is an integer 1, 2 or 3, it is to be understood that the substituent or substituents R$^5$ may be present on any suitable carbon atom in —Alk. Where more than one R$^5$ substituent is present these may be the same or different and may be present on the same or different atom in —Alk or in R$^5$ as appropriate. Thus for example, —Alk(R$^5$)$_m$ may represent a —CH(R$^5$)$_2$ group, such as a —CH(OH)Ar$^2$ group where Ar$^2$ is an aryl or heteroaryl group as defined below. Clearly, when m is zero and no substituent R$^5$ is present the alkylene, alkenylene or alkynylene chain represented by Alk becomes an alkyl, alkenyl or alkynyl group.

When R$^5$ is a substituted amino group it may be for example a group —NHR$^6$ [where R$^6$ is as defined above] or a group —N[R$^6$]$_2$ wherein each R$^6$ group is the same or different.

When R$^5$ is a halogen atom it may be for example a fluorine, chlorine, bromine, or iodine atom.

When R$^5$ is a substituted hydroxyl or substituted thiol group it may be for example a group —OR$^6$ or —SR$^6$ respectively.

Esterified carboxyl groups represented by the group R$^5$ include groups of formula —CO$_2$Alk$^1$ wherein Alk$^1$ is a straight or branched, optionally substituted $C_{1-8}$ alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-2}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the Alk$^1$ group include R$^5$ substituents described above.

When Alk is present in or as a substituent, it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^7$)— groups.

Cycloalkyl groups represented by the group R$^5$ include $C_{5-7}$ cycloalkyl groups such as cyclopentyl or cyclohexyl groups.

Heterocycloalkyl groups represented by the group $R^5$ include optionally substituted heteroC$_{3-6}$cycloalkyl groups containing one or two oxygen, sulphur or nitrogen containing groups as described above in relation to the group $R^3$.

Aryl and heteroaryl groups represented by the groups $R^5$, $R^6$ or $Ar^2$ include for example optionally substituted monocyclic or bicyclic $C_{6-12}$ aromatic groups such as optionally substituted phenyl, 1- or 2-naphthyl groups, or optionally substituted monocyclic or bicyclic $C_{1-9}$ heteroaromatic groups such as optionally substituted pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, phthalazinyl, quinoxalinyl, cinnolinyl, naphthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl and 5,6,7,8-tetrahydroisoquinolyl, purinyl, or pteridinyl groups. Optional substituents which may be present on these aromatic and heteroaromatic groups include those optional substituents described above in relation to the group $R^4$, but excluding optionally substituted aromatic groups.

Particularly useful atoms or groups represented by $R^5$, or Alk($R^5$)$_m$ as appropriate, include fluorine, chlorine, bromine or iodine atoms, or $C_{1-6}$ alkyl, e.g. methyl or ethyl, $C_{1-6}$ alkylamino, e.g. methylamino or ethylamino, $C_{1-6}$hydroxyalkyl, e.g. hydroxymethyl or hydroxyethyl, $C_{1-6}$ alkylthiol e.g. methylthiol or ethylthiol, $C_{1-6}$alkoxy, e.g. methoxy, ethoxy, n-propoxy or n-butoxy, halo$C_{1-6}$alkoxy, e.g. trifluoromethoxy, $C_{5-7}$cycloalkoxy, e.g. cyclopentyloxy, halo$C_{1-6}$alkyl, e.g. trifluoromethyl, $C_{1-6}$alkylamino, e.g. methylamino or ethylamino, amino (—NH$_2$), amino$C_{1-6}$ alkyl, e.g. aminomethyl or aminoethyl, $C_{1-6}$dialkylamino, e.g. dimethylamino or diethylamino, $C_{1-6}$dialkylamino$C_{1-6}$alkoxy, e.g. dimethylaminoethoxy or diethylaminoethoxy, imido, such as phthalimido or naphthalimido, e.g. 1,8-naphthalimido, 1,1,3-trioxo-benzo[d]thiazolidino, nitro, cyano, hydroxyl (—OH), formyl [HC(O)—], carboxyl (—CO$_2$H), —CO$_2$Alk$^1$ [where Alk$^1$ is as defined above], $C_{1-6}$ alkanoyl, e.g. acetyl, thiol (—SH), thio$C_{1-6}$ alkyl, e.g. thiomethyl or thioethyl, —SC(NH)NH$_2$, phenoxy, sulphonyl (—SO$_3$H), $C_{1-6}$ alkylsulphonyl, e.g. methylsulphonyl, aminosulphonyl (—SO$_2$NH$_2$), $C_{1-6}$ alkylaminosulphonyl, e.g. methylaminosulphonyl or ethylaminosulphonyl, $C_{1-6}$dialkylamino-sulphonyl, e.g. dimethylaminosulphonyl or diethylaminosulphonyl, phenylaminosulphonyl, carboxamido (—CONH$_2$), $C_{1-6}$alkylaminocarbonyl, e.g. methylaminocarbonyl or ethylaminocarbonyl, $C_{1-6}$ dialkylaminocarbonyl, e.g. dimethylaminocarbonyl or diethylaminocarbonyl, sulphonylamino (—NHSO$_2$H), $C_{1-6}$ alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, e.g. 2-, 3- or 4-substituted phenylsulphonylamino such as 2-nitrophenylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonyl-amino, e.g. dimethylaminosulphonylamino or diethylaminosulphonylamino, phenylaminosulphonylamino, aminocarbonylamino, $C_{1-6}$ alkylaminocarbonylamino e.g. methylaminocarbonylamino or ethylaminocarbonyl-amino, $C_{1-6}$dialkylaminocarbonylamino, e.g. dimethylaminocarbonylamino or diethylaminocarbonylamino, phenylaminocarbonylamino, $C_{1-6}$alkanoylamino, e.g. acetylamino, $C_{1-6}$alkanoylamino$C_{1-6}$alkyl, e.g. acetylamino-methyl, $C_{1-6}$ alkoxycarbonylamino, e.g. methoxycarbonylamino, ethoxy-carbonylamino or t-butoxycarbonylamino, or optionally substituted heteroC$_{3-6}$cycloalkyl, e.g. piperidinyl, piperazinyl, 3-methyl-1-piperazinyl, homopiperazinyl or morpholinyl groups.

Where desired, two $R^5$ or —Alk($R^5$)$_m$ substituents may be linked together to form a cyclic group such as a cyclic ether, e.g. a $C_{1-6}$alkylenedioxy group such as methylenedioxy or ethylenedioxy.

It will be appreciated that where two or more $R^5$ or —Alk($R^5$)$_m$ substituents are present, these need not necessarily be the same atoms and/or groups.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

It will be appreciated that depending on the nature of the group Ar and the substituents $R^2$ and $R^3$, the compounds of formula (1) may exist as geometrical isomers and/or may have one or more chiral centres so that enantiomers or diasteromers may exist. It is to be understood that the invention extends to all such isomers of the compounds of formula (1), and to mixtures thereof, including racemates.

One preferred class of compounds of formula (1) is that wherein the pyrimidine group is attached to the pyridyl group to yield a compound of formula (1a):

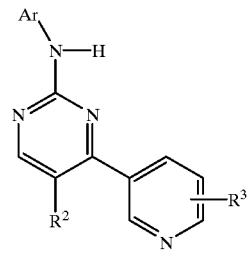

(1a)

and the salts, solvates, hydrates and N-oxides thereof.

Preferred compounds of this type are those of formula (1b):

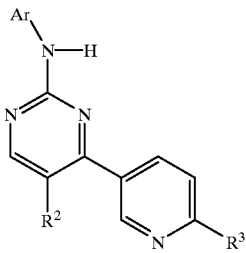

and the salts, solvates, hydrates and N-oxides thereof.

In the compounds of formulae (1), (1a) or (1b) $R^2$ is preferably a hydrogen atom.

In the compounds according to the invention the aromatic group represented by Ar is preferably an optionally substituted phenyl group. The optional substituent(s) may be any of those $R^5$ or $—Alk(R^5)_m$ atoms or groups generally or particularly described above or in the Examples hereinafter. Particularly useful substituents include one, two or three $R^5$ or $—Alk(R^5)_m$ substituents present at any position in the phenyl ring, especially at the 3-, 4- and/or 5-positions relative to the carbon atom attached to the remainder of the compound of the invention.

In one particular preference, $R^3$ in compounds of formulae (1), (1a) or (1b) is a piperazine or homopiperazine group, optionally substituted by one or two $R^4$ substituents as described above. Preferably, the $R^3$ piperazine or homopiperazine group is attached to the rest of the molecule of formula (1) through one of its nitrogen atoms. The piperazine or homopiperazine group is preferably disubstituted or is especially a monosubstituted group. When the piperazine or homopiperazine is monosubstituted and is attached to the remainder of the molecule of formula (1) through one of ifs nitrogen atoms then the substituent ($R^4$) is preferably attached to the other free ring nitrogen atom. Especially useful $R^4$ substituents are those particularly mentioned above and include for example optionally substituted $C_{1-6}$alkyl, $C_{1-6}$ alkoxy, —OH—, —NH$_2$, —NHCH$_3$, —N(CH$_3$)$_2$, —SO$_2$NR$^{1a}$R$^{1b}$, or optionally substituted phenyl groups especially those groups of these types specifically described above or in the Examples hereinafter.

Preferred compounds according to the invention include the compounds specifically described in the Examples hereinafter.

Compounds according to the invention are potent and selective inhibitors of the protein tyrosine kinases ZAP-70 and syk, as demonstrated by differential inhibition of ZAP-70 and/or syk and other kinases such as cdc2 kinase, EGFr kinase, p56$^{lck}$ kinase, protein kinase C, csk kinase and p59$^{fyn}$ kinase. The ability of the compounds to act in this way may be simply determined by employing tests such as those described in the Examples hereinafter.

The compounds according to the invention are thus of particular use in the prophylaxis and treatment of disease in which inappropriate activation of ZAP-70 or syk plays a role. Such diseases include those in which inappropriate activation of T-cells, B-cells, mast cells or platelets is present or in which eosinophilia is a feature. Examples of these diseases include autoimmune diseases, such as rheumatoid arthritis, multiple sclerosis, systemic lupus erythematosus and psoriasis; graft v host disease and other transplantation associated rejection events; and allergic diseases such as asthma, atopic dermatitis, allergic rhinitis and allergic conjunctivitis. The compounds are also of use in the reduction of complications following percutaneous transluminal coronary angioplasty, in the prophylaxis and treatment of thrombosis of the major organs, deep vein thrombosis and peripheral vascular disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols Ar, $R^2$, $R^3$, $R^4$, Alk, $Alk^1$, Ar and $Ar^1$ when used in the text or formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) may be prepared by reaction of a guanidine of formula (2):

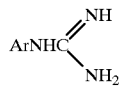

(2)

or a salt thereof with an enaminone of formula (3):

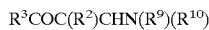

(3)

where $R^9$ and $R^{10}$, which may be the same or different is each a $C_{1-6}$ alkyl group.

The reaction may be performed in a solvent, for example a protic solvent such as an alcohol, e.g. ethanol, methoxyethanol or propanol, optionally in the presence of a base e.g. an alkali metal base, such as sodium hydroxide or potassium carbonate, at an elevated temperature, e.g. the reflux temperature.

Salts of the compounds of formula (2) include acid salts such as inorganic acid salts e.g. hydrochlorides or nitrates.

Intermediate guanidines of formula (2) may be prepared by reaction of the corresponding amine $ArNH_2$ with cyanamide at an elevated temperature. The reaction may be performed in a solvent such as ethanol at an elevated temperature, e.g. up to the reflux temperature. Where it is desired to obtain a salt of a guanidine of formula (2), the reaction may be performed in the presence of a concentrated acid, e.g. hydrochloric or nitric acid.

The amines $ArNH_2$ are either known compounds or may be obtained by conventional procedures, for example by hydrogenation of the corresponding nitro derivatives using for example hydrogen in the presence of a metal catalyst in a suitable solvent, for example as more particularly described in the interconversion reactions discussed below. The nitrobenzenes for this particular reaction are either known compounds or may be prepared using similar methods to those used for the preparation of the known compounds.

Intermediate enaminones of formula (3) are either known compounds or may be prepared by reaction of an acetyl derivative $R^3COCH_2R^2$ with an acetal $(R^9)(R^{10})NCH(OCH_3)_2$ at an elevated temperature. The starting materials for this reaction are either known compounds of may be prepared by methods analogous to those used for the preparation of the known compounds.

In another process according to the invention, a compound of formula (1) may be prepared by displacement of a leaving atom or group in a pyrimidine of formula (4):

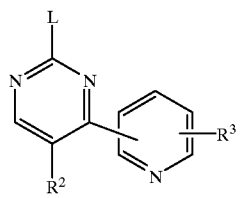

(4)

[where L is a leaving atom or group], with an amine $ArNH_2$.

The reaction may be performed at an elevated temperature, for example the reflux temperature, where necessary in the presence of a solvent, for example an alcohol, such as 2-ethoxyethanol or an aromatic hydrocarbon such as toluene or mesitylene optionally in the presence of a base for example an amine such as pyridine. Where desired, the reaction may also be performed on an intermediate of formula (4) which is linked, for example via its $R^3$ group, to a solid support, such as a polystyrene resin. After the reaction, the desired compound of formula (1) may be displaced from the support by any convenient method, depending on the original linkage chosen. Particular examples of such solid-phase syntheses are given in the Examples hereinafter.

Particular examples of leaving atoms or groups represented by L in compounds of formula (4) include halogen atoms such as a chlorine or bromine atom, and sulphonyloxy groups, for example alkylsulphonyloxy groups such as a methylsulphonyloxy group.

Intermediate pyrimidines of formula (4) may be prepared by cross-coupling a pyrimidine of formula (5):

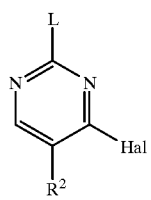

(5)

[where Hal is a halogen atom] with a pyridine of formula (6):

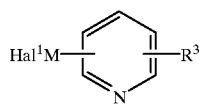
(6)

[where Hal¹ is a halogen atom such as a chlorine atom, and M is a metal atom, such as a zinc atom].

The reaction may be carried out in the presence of a metal catalyst, for example a metal complex catalyst such as a palladium complex, e.g. tetrakis(triphenylphosphine) palladium, in a solvent such as an ether, e.g. a cyclic ether such as tetrahydrofuran, at an elevated temperature, e.g. the reflux temperature.

Intermediates of formula (6) may be prepared by conventional procedures, for example, where M is a zinc atom, by reaction of a halide of formula (7):

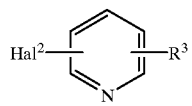
(7)

[where Hal² is for example a bromine atom] with tert-butyllithium at a low temperature e.g. around −100° C. followed by reaction with a zinc salt, e.g. zinc chloride at a low temperature, e.g. around −75° C. Both reactions may be carried out in a solvent such as an ether, e.g. tetrahydrofuran. Any reactive groups in $R^3$ not involved in this or the above-described coupling reaction may need to be in a protected form, the protecting group being removed prior to, during or subsequent to the displacement reaction involving the pyrimidines of formula (4).

The halide starting materials of formula (7) may be prepared by displacement of a leaving group from a pyridine of formula (8):

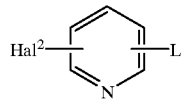
(8)

[where L is a leaving group as described above] using a nucleophilic reagent $R^3H$. The reaction may be performed as described above in relation to the preparation of compounds of formula (1) from the intermediate pyrimidines of formula (4).

Intermediates of formulae (5) and (8) are either known compounds or may be prepared using methods analogous to those used for the preparation of the known compounds.

In another example of a displacement reaction according to the invention a compound of formula (1) wherein $R^3$ is an optionally substituted heterocycloalkyl group containing a ring nitrogen atom attached to the remainder of the molecule of formula (1), may be prepared by reaction of a pyrimidine of formula (9):

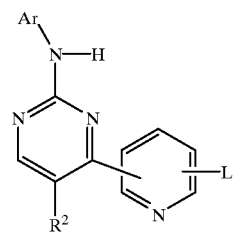
(9)

[where L is a leaving group as previously described], with a heterocyclic amine $R^{3a}NH$ [where $R^{3a}N$ is an optionally substituted heterocycloalkyl group $R^3$ containing at least one nitrogen atom.]

The reaction may be performed as described above in relation to the preparation of compounds of formula (1) from the intermediate pyrimidines of formula (4). The intermediate amines $R^{3a}NH$ are either known compounds or may be prepared from known compounds for example by the simple interconversion reactions described for the groups Ar and/or $R^3$ in the text or Examples hereinafter.

The intermediate pyrimidines of formula (9) may be prepared from the corresponding guanidine of formula (2) and an enaminone of formula (10):

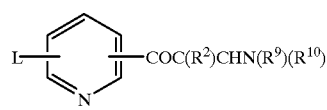
(10)

using the conditions described above for the reaction of intermediates of formulae (2) and (3). The enaminones of formula (10) may be prepared using an appropriate acetyl derivative of formula (11):

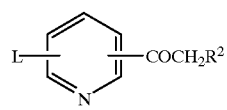
(11)

with an acetal $(R^9)(R^{10})NCH(OCH_3)_2$ as described previously for the preparation of enaminones of formula (3).

Compounds of formula (1) may also be prepared by interconversion of other compounds of formula (1) and it is to be understood that the invention extends to such interconversion processes. Thus, for example, standard substitution approaches employing for example alkylation, arylation, heteroarylation, acylation, thioacylation, sulphonylation, formylation or coupling reactions may be used to add new substitutents to and/or extend existing substituents in compounds of formula (1). Alternatively existing substituents in compounds of formula (1) may be modified by for example oxidation, reduction or cleavage reactions to yield other compounds of formula (1).

The following describes in general terms a number of approaches which can be employed to modify existing Ar and/or $R^3$ groups in compounds of formula (1). It will be appreciated that each of these reactions will only be possible where an appropriate functional group exists in a compound of formula (1).

Thus, for example alkylation, arylation or heteroarylation of a compound of formula (1) may be achieved by reaction of the compound with a reagent $R^4L$, AlkL, $Ar^1L$ or $Ar^2L$ where L is a leaving atom or group as described above. The reaction may be carried out in the presence of a base, e.g. an inorganic base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at around 0° C. to around 40° C.

In a variation of this process the leaving group L may be alternatively part of the compound of formula (1) and the reaction performed with an appropriate nucleophilic reagent at an elevated temperature. Where appropriate the reaction may be performed in a solvent such as an alcohol, e.g. ethanol.

In another general example of an interconversion process, a compound of formula (1) may be acylated or thioacylated. The reaction may be performed for example with an acyl halide or anhydride in the presence of a base, such as a tertiary amine e.g. triethylamine in a solvent such as a halogenated hydrocarbon, e.g. dichloromethane at for example ambient temperature, or by reaction with a thioester in an inert solvent such as tetrahydrofuran at a low temperature such as around 0° C. The reaction is particularly suitable for use with compounds of formula (1) containing primary or secondary amino groups.

In a further general example of an interconversion process, a compound of formula (1) may be formylated, for example by reaction of the compound with a mixed anhydride $HCOOCOCH_3$ or with a mixture of formic acid and acetic anhydride.

Compounds of formula (1) may be prepared in another general interconversion reaction by sulphonylation, for example by reaction of a compound of formula (1) with a reagent $AlkS(O)_2L$, or $Ar^1S(O)_2L$ in the presence of a base, for example an inorganic base such as sodium hydride in a solvent such as an amide, e.g. a substituted amide such as dimethylformamide at for example ambient temperature. The reaction may in particular be performed with compounds of formula (1) possessing a primary or secondary amino group.

In another example, a compound of formula (1) may be prepared by sulphamoylation, for example by reaction of a compound of formula (1) where, for example $R^3$ contains an available nitrogen atom, with a reagent $R^{1a}R^{1b}NSO_2L$ in the presence of a solvent, e.g. an organic amine such as triethylamine at around ambient temperature.

In further examples of interconversion reactions according to the invention compounds of formula (1) may be prepared from other compounds of formula (1) by modification of existing functional groups in the latter.

Thus in one example, ester groups —$CO_2Alk^1$ in compounds of formula (1) may be converted to the corresponding acid [—$CO_2H$] by acid- or base-catalysed hydrolysis or by catalytic hydrogenation depending on the nature of the group $Alk^1$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol. Catalytic hydrogenation may be carried out using for example hydrogen in the presence of a metal catalyst, for example palladium on a support such as carbon in a solvent such as an ether, e.g. tetrahydrofuran or an alcohol, e.g. methanol.

In a second example, —$OAlk^2$ [where $Alk^2$ represents an alkyl group such as a methyl group] groups in compounds of formula (1) may be cleaved to the corresponding alcohol —OH by reaction with boron tribromide in a solvent such as a halogenated hydrocarbon, e.g. dichloromethane at a low temperature, e.g. around $-78°$ C.

In another example, alcohol —OH groups in compounds of formula (1) may be converted to a corresponding —OAlk or —OAr group by coupling with a reagent AlkOH or ArOH in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in compounds of formula (1) may be obtained, in another example, by reaction of a corresponding amine [—$NH_2$] with sulphamide in the presence of an organic base such as pyridine at an elevated temperature, e.g. the reflux temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation as just described, or by chemical reduction using for example a metal, e.g. tin or iron, in the presence of an acid such as hydrochloric acid.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Where salts of compounds of formula (1) are desired, these may be prepared by conventional means, for example by reaction of a compound of formula (1) with an appropriate acid or base in a suitable solvent or mixture of solvents, e.g. an organic solvent such as an ether, e.g. diethylether, or an alcohol, e.g. ethanol.

The following Examples illustrated the invention. In the Examples all $^1$Hnmr were run at 300 MHz unless specified otherwise. All temperatures are in ° C. The following abbreviations are used: DMSO—dimethylsulphoxide; DMF—dimethylformamide; THF—tetrahydrofuran. Intermediates used in the Examples are:

Intermediate 1: 4-(2-chloropyridin-5-yl)-N-(3,4,5-trimethoxyphenyl)-2-pyrimidineamine.

Intermediate 2: 1-(2-chloropyridin-5-yl)-3-dimethylamino-2-propen-1-one.

The preparations of both Intermediates are described in Example 1.

EXAMPLE 1

4-(2-(Piperazin-1-yl)pyridin-5-yl)-N-(3,4,5-trimethoxyphenyl)-2-pyrimidineamine

A mixture of Intermediate 1 (300 mg, 0.81 mmol) and piperazine (142 mg, 1.65 mmol) was heated as a melt at 140° for 1.5 h. On cooling to room temperature the mixture was partitioned between dichloromethane and water, dried ($MgSO_4$) and concentrated under reduced pressure. The residue was subjected to column chromatography [silica methanol-dichloromethane-25% aq.ammonia 10:90:1] to afford the title compound (275 mg), after trituration with ether, as an off-white solid m.p. 134–135°. δH ($d^6$DMSO) 9,39 (1H, s), 8.92 (1H, d, 2.0 Hz), 8.42 (1H, d, J 5.0 Hz), 8.24 (1H, d, 8.0 Hz), 7.28–7.25 (3H, m), 6.90 (1H, d, J 8.0 Hz), 3.78 (6H s), 3.64 (3H, s), 3.59–3.54 (4H, m), 2.81–2.75 (4H, m) and 2.38 (1H, br s).

Intermediate 1 was prepared by heating a solution of 3,4,5-trimethoxyphenylguanidine (6.42 g, 22.3 mmol), Intermediate 2 (4.70 g, 22.33 mmol) and powdered sodium hydroxide in propan-2-ol at reflux for 3.5 h. The solvent was removed under reduced pressure and the residue subjected to column chromatography [silica, 25% hexane-ethyl acetate] to afford the desired product (1.43 g) as a yellow solid m.p. 191–192°. δH (d⁶DMSO) 9.63 (1H, s), 9.17 (1H, d, J 2.0 Hz), 8.60 (1H, d, J 5.1 Hz), 8.55 (1H, dd, J 8.4, 2.5 Hz), 7.71 (1H, d, J 8.4 Hz), 7.48 (1H, d, J 5.1 Hz), 7.24 (2H, s), 3.77 (6H, s) and 3.62 (3H, s).

Intermediate 2 was prepared by heating a solution of 5-acetyl-2-chloropyridine (4.50 g 28.9 mmol) in dimethylformamide diethylacetal (15 ml) under reflux for 1 h. On cooling the resulting solid was collected by filtration and washed with ether and hexane to give the enaminone (5.07 g) as an orange solid m.p. 130–132°. δH (d⁶DMSO) 8.87 (1H, d, J 2.0 Hz), 8.25 (1H, dd, J 8.3, 5.2 Hz), 7.76 (1H, d, J 12.2 Hz), 7.55 (1H, dd, J 8.3, 0.6 Hz), 5.84 (1H, d, J 12.2 Hz), 3.15 (3H, br s) and 2.93 (3H, br s).

5-Acetyl-2-chloropyridine was prepared by the addition of dimethyl malonate (17.2 ml, 150 mmol) to a suspension of magnesium chloride (anhydrous) in toluene (200 ml) and triethylamine (39.5 ml) at room temperature. After the suspension had been stirred for 1.5 h, 6-chloronicotinyl chloride in toluene (200 ml) was added dropwise over 20 min, after which the mixture was sitrred for an additional 1.5 h. After slow addition of concentrated hydrochloric acid (37 ml), the toluene layer was decanted, dried (MgSO₄) and concentrated under reduced pressure. The residue was dissolved in anhydrous DMSO (50 ml), heated to 150°, water (3.5 ml) added dropwise and heating continued for 1 h. Water (400 ml) was added, and the resulting solution extracted with diethyl ether (300 ml). The ether layer was washed with water (150 ml) dried (MgSO₄) and concentrated under reduced pressure to give the desired product (16.0 g) as a pale yellow solid m.p. 103°. δH (CDCl₃) 8.90 (1H, d, J 2.8 Hz), 8.18 (1H, dd, J 10.0, 4.8 Hz), 7.42 (1H, d, J 10.0 Hz) and 2.61 (3H, s).

The following compounds of Examples 2–26 were prepared in a similar manner to the compound of formula (1) using Intermediate 1 as one starting material.

EXAMPLE 2

4-(2-(1,4-Diazacycloheptan-1-yl)pyridin-5-yl)-N-(3,4,5-trimethoxyphenyl)-2-pyrimidineamine From Intermediate 1 (300 mg, 0.81 mmol) and homopiperazine (600 mg, 6 mmol) to give the title compound (310 mg) as a yellow solid m.p.144–145°. δH (d⁶DMSO) 9.35 (1H, s), 8.88 (1H, d, J 2.3 Hz), 8.38 (1H, d, J 5.2 Hz), 8.22 (1H, dd, J 9.0, 2.4 Hz), 7.26–7.24 (3H, m), 6.74 (1H, d, J 9.0 Hz), 3.77 (6H, s), 3.76–3.64 (4H, m), 3.62 (3H, s), 2.86–2.83 (2H, m), 2.67–2.63 (2H, m) and 1.77–1.73 (2H, m).

EXAMPLE 3

4-(2-(4-Methylpiperazin-1-yl)pyridin-5-yl)-N-(3,4,5-trimethoxyphenyl)-2-pyrimidineamine From Intermediate 1 (200 mg, 0.54 mmol) and 1-methylpiperazine (400 mg, 4 mmol) to give the title compound (210 mg) as an off-white solid 178–179°. δH (d⁶DMSO) 9.39 (1H, s), 8.91 (1H, d, J 2.3 Hz), 8.41 (1H, d, J 5.3 Hz), 8.26 (1H, dd, J 9.0, 2.3 Hz), 7.29–7.25 (3H, m), 6.94 (1H, d, J 9.1 Hz), 3.77 (6H, s), 3.62–3.60 (7H, m), 2.40–2.37 (4H, m) and 2.20 (3H, s).

EXAMPLE 4

4-(2-(3-(R,S)-Methylpiperazin-1-yl)pyridin-5-yl)-N-(3,4,5-trimethoxyphenyl)-2-pyrimidineamine From Intermediate 1 (700 mg, 1.89 mmol) and 2(R,S)-methylpiperazine (1.0 g, 10 mmol) to give the title compound (300 mg) as a pale yellow solid m.p. 138–139°. δH (CDCl₃) 8.87 (1H, d, J 2.1 Hz), 8.37 (1H, d, J 5.3 Hz), 8.21 (1H, dd, J 9.0, 2.5 Hz), 7.21 (1H, s), 7.03 (1H, d, J 5.3 Hz), 7.01 (2H, s), 6.67 (1H, d, J 9.0 Hz), 4.33–4.13 (2H, m), 3.89 (6H, s), 3.83 (3H, s), 3.16–3.13 (1H, m), 3.03–2.88 (3H, m), 2.65–2.57 (1H, m), 1.98 (1H, br s) and 1.18 (3H, d, J 6.2 Hz).

EXAMPLE 5

4-(2-(3(S)-Methylpiperazin-1-yl)pyridin-5-yl)-N-(3,4,5-trimethoxyphenyl)-2-pyrimidineamine From Intermediate 1 (740 mg, 2.0 mmol) and 2(S)-methylpiperazine (7.50 mg, 7.5 mmol) to give the title compound (670 mg) as a yellow solid m.p. 139–140°. δH (CDCl₃) 8.87 (1H, d, J 2.2 Hz), 8.37 (1H, d, J 5.3 Hz), 8.21 (1H, dd, J 9.0, 2.4 Hz), 7.33 (1H, s), 7.03 (1H, d, J 5.3 Hz), 7.01 (2H, s), 6.66 (1H, d, J 9.0 Hz), 4.32–4.24 (2H, m), 3.89(6H, s), 3.83 (3H, s), 3.16–3.13 (1H, m), 3.03–2.89 (3H, m), 2.65–2.57 (1H, m), 2.19 (1H, br s) and 1.18 (3H, d, J 6.2 Hz).

EXAMPLE 6

4-(2-(3(R)-Methylpiperazin-1-yl)pyridin-5-yl)-N-(3,4,5-trimethoxyphenyl)-2-pyrimidineamine From Intermediate 1 (740 mg, 2.0 mmol) and 2(R)-methylpiperazine (750 mg, 7.5 mmol) to give the title compound (560 mg) as a yellow solid m.p. 138–139°. δH (CDCl₃) 8.87 (1H, d, J 2.2 Hz), 8.37 (1H, d, J 5.3 Hz), 8.20 (1H, dd, J 9.0, 2.4 Hz), 7.33 (1H, s), 7.03 (1H, d, J 5.3 Hz), 7.01 (2H, s), 6.67 (1H, d, J 9.0 Hz), 4.32–4.24 (2H, m), 3.89 (6H, s), 3.03 (3H, s), 3.16–3.13 (1H, m), 3.03–2.89 (3H, m), 2.65–2.57 (1H, m) and 1.18 (3H, d, J 6.2 Hz).

EXAMPLE 7

4-(2-(4-Ethylpiperazin-1-yl)pyridin-5-yl)-N-(3,4,5-trimethoxyphenyl)-2-pyrimidineamine From Intermediate 1 (350 mg, 0.945 mmol) and 1-ethylpiperazine (457 mg, 4 mmol) to give the title compound (400 mg) as an off-white solid m.p. 139–390°. δH (CDCl₃) 8.87 (1H, d, J 2.0 Hz), 8.37 (1H, d, J 5.3 Hz), 8.21 (1H, dd, J 9.0. 2.5 Hz), 7.18 (1H, s), 7.04 (1H, d, J 5.3 Hz), 7.01 (2H, s), 6.68 (1H, d, J 9.0 Hz), 3.90 (6H, s), 3.84 (3H, s), 3.70 (4H, m), 2.57 (4H, m), 2.48 (2H, q, J 7.2 Hz) and 1.14 (3H, t, J 7.2).

EXAMPLE 8

4-(2-(3,5-Dimethylpiperazin-1-yl)pyridin-5-yl)-N-(3,4,5-trimethoxyphenyl)-2-pyrimidineamine From Intermediate 1 (350 mg, 0.85 mmol) and 2,6-dimethylpiperazine (500 mg, 4.4 mmol) to give the title compound (180 mg) as a yellow solid m.p.110–111°. δH (CDCl₃) 8.86 (1H, d, J 2.0 Hz), 8.36 (1H, d, J 5.3 Hz), 8.21 (1H, dd, J 9.0, 2.5 Hz), 7.20 (1H, br s), 7.03 (1H, d, J 5.3 Hz), 7.01 (2H, s), 6.68 (1H, d, J 9.0 Hz), 4.28 (2H, dd, J 2.8, 2.3 Hz), 3.90 (6H, s), 3.84 (3H, s), 2.98–2.92 (2H, m), 2.50 (2H, dd, J 12.6, 10.6 Hz), 1.69 (1H, br s) and 1.17 (6H, d, J 6.3 Hz).

EXAMPLE 9

4(-2(3-Hydroxymethylpiperazin-1-yl)pyridin-5-yl)-N-(3,4,5-trimethoxyphenyl)-2-pyrimidineamine From Intermediate 1 (740 mg, 2 mmol) and 3-piperazinemethanol (800 mg, 6.89 mmol) to give the title compound (580 mg) as a yellow solid m.p. 118–119°. δH (CDCl₃) 8.86 (1H, d, J 2.2 Hz), 8.37 (1H, d, J 5.3 Hz), 8.20 (1H, dd, J 9.0, 2.5 Hz), 7.27 (1H, s), 7.03 (1H, d, J 5.3 Hz), 7.01 (2H, s), 6.68 (1H, d, J 9.0 Hz), 4.25–4.18 (2H, m), 3.89 (6H, s), 3.84 (3H, s), 3.75 (1H, dd, J 10.8, 4.1 Hz), 3.62 (1H, dd, J 10.8, 6.3 Hz), 3.20–2.91 (5H, m) and 2.13 (2H, brs).

EXAMPLE 10

4-(2-(3-N,N-Dimethylaminomethylpiperazin-1-yl)pyridin-5-yl)-N-(3,4,5-trimethoxyphenyl)-2-pyrimidineamine From Intermediate 1 (400 mg, 1.08 mmol) and 2-dimethylaminomethylpiperazine (500 mg, 3.5 mmol) to give the title compound (360 mg) as a yellow solid m.p. 86–87°. δH (CDCl₃) 8.87 (1H, d, J 2.2 Hz), 8.36 (1H, d, J 5.3 Hz), 8.20 (1H, dd, J 9.0, 2.2 Hz), 7.27 (1H, s), 7.03 (1H, d, J 5.3 Hz), 7.01 (2H, s), 6.68 (1H, d, J 9.0 Hz), 4.25 (2H, 6t, J 13 Hz), 3.89 (6H, s), 3.83 (3H, s), 3.16–3.02 (2H, m), 2.93–2.83 (2H, m), 2.64 (1H, dd, J 12.3, 10.2 Hz), 2.40 (1H, dd, J 12.1, 9.7 Hz), 2.26 (6H, s), 2.23–2.21 (1H, m) and 2.12 (1H, s).

EXAMPLE 11

4-(2-(3(R)-(Prop-2-yl)piperazin-1-yl)pyridine-5-yl)-N-(3,4,5-trimethoxyphenyl)-2-pyrimidineamine From Intermediate 1 (555 mg, 1.5 mmol) and 2(R)-(prop-2-yl)piperazine (641 mg, 5 mmol) to give the title compound (280 mg) as a yellow solid m.p. 91° (decomp). δH (CDCl₃) 8.89 (1H, d, J 2.4 Hz), 8.37 (1H, d, J 5.3 Hz), 8.21 (1H, dd, J 9.0, 2.4 Hz), 7.18 (1H, s), 7.04 (1H, d, J 5.3 Hz), 7.02 (2H, s), 6.67 (1 H, d, J 9.0 Hz), 4.38 (1H, bd, J 12.5 Hz), 4.24 (1H, bd, J 12.5 Hz), 3.90 (6H, s), 3.84 (3H, s), 3.18 (1H, m), 2.99–2.88 (2H, m), 2.74–2.66 (1H, m), 2.51–2.48 (1H, m), 1.76 (1H, br s), 1.72–1.69 (1H, m), 1.04 (3H, d, J 6.7 Hz) and 1.02 (3H, d, J 6.7 Hz).

EXAMPLE 12

4-(2-(4-(4-Nitrophenyl)piperazin-1-yl)pyridin-5-yl)N-(3,4,5-trimethoxyphenyl)-2-pyrimidineamine From Intermediate 1 (350 mg, 0.95 mmol) and 1-(4-nitrophenyl)piperazine (415 mg, 2 mmol) to give the title compound (220 mg) as a yellow solid m.p, 222–223°. δH (CDCl₃) 8.92 (1H, s), 8.39 (1H, d, J 5.3 Hz), 8.26 (1H, d, J 9.0 Hz), 8.17 (2H, d, J 9.3 Hz), 7.11 (1H, s), 7.06 (1H, d, J 5.3 Hz), 7.02 (2H, s), 6.85 (2H, d, J 9.3 Hz), 6.71 (1H, d, J 9.0 Hz), 3.91–3.89 (10 H, m), 3.84 (3H, s) and 3.65–3.61 (4H, m).

EXAMPLE 13

4-(2-(4-(3-Hydroxypropyl)piperazin-1-yl)pyridin-5-yl)-N-(3,4,5-trimethoxyphenyl)-2-pyrimidineamine From Intermediate 1 (700 mg, 1.89 mmol) and 1-(3-hydroxypropyl)piperazine (1.09 g, 7 mmol) to give the title compound (750 mg) as a yellow solid m.p.116–117°. δH (CDCl₃) 8.88 (1h, d, J 2.2 Hz), 8.37 (1H, d, J 5.3 Hz), 8.21 (1H, dd, J 9.0, 2.5 Hz), 7.20 (1H, s), 7.03 (1H, d, J 5.3 Hz), 7.01 (2H, s), 6.67 (1H, d, J 9.0 Hz), 3.89 (6H, s), 3.86–3.80 (4H, m), 3.83 (3H, s), 3.70–3.67 (4H, m), 2.69–2.63 (4H, m) and 1.80–1.78 (2H, m).

EXAMPLE 14

4-(2-(3-(2-Hydroxyethyl)piperazin-1-yl)pyridin-5-yl)-N-(3,4,5-trimethoxyphenyl)-2-pyrimidineamine From Intermediate 1 (740 mg, 2 mmol) and 2-(2-hydroxyethyl)piperazine (800 mg, 6.15 mmol) to give the title compound (450 mg) as a yellow solid m.p. 150–151°.

δH (CDCl₃) 8.86 (1H, d, J 2.3 Hz), 8.37 (1H, d, J 5.2 Hz), 8.21 (1H, dd, J 9.0, 2.4 Hz), 7.18 (1H, s), 7.03 (1H, d, J 5.3 Hz), 7.01 (2H, s), 6.68 (1H, d, J 9.0 Hz), 4.40–4.22 (2H, m), 3.90–3.85 (2H, m), 3.89 (6H, s), 3.25–3.09 (4H, m), 2.98–2.92 (3H, m) and 1.89–1.83 (2H, m).

EXAMPLE 15

4-(2-(4-(2-Aminoethyl)piperazin-1-yl)pyridin-5-yl-)N-(3,4,5-trimethoxyphenyl)-2-pyrimidineamine From Intermediate 1 (750 mg, 2.02 mmol)) and 1-(2-aminoethyl)piperazine (1.04 g, 8 mmol) to give the title compound (405 mg) as a white solid m.p. 88–89°. δH (CDCl₃) 8.87 (1H, d, J 2.1 Hz), 8.37 (1H, d, J 5.4 Hz), 8.21 (1H, dd, J 9.0, 3.4 Hz), 7.12 (1H, s), 7.05–7.02 (3H, m), 6.67 (1H, d, J 9.0 Hz), 3.90 (6H, s), 3.84 (3H, s), 3.71–3.67 (4H, m), 2.85 (2H, t, J 5.0 Hz), 2.60–2.56 (4H,m) and 2.49 (2H, t, J 6.0 Hz).

EXAMPLE 16

4-(2-(4-(2-Hydroxyethyl)piperazin-1-yl)pyridin-5-yl)-N-(3,4,5-trimethoxyphenyl)-2-pyrimidineamine From Intermediate 1 (300 mg, 0.81 mmol) and 1-(2-hydroxyethyl)piperazine (524 mg, 4.0 mmol) to give the title compound (263 mg) as an off-white solid m.p. 156–157°. δH (CDCl₃) 8.88 (1H, d, J, 2.3 Hz), 8.37 (1H, d, J 5.3 Hz), 8.21 (1H, dd, J 9.0, 2.5 Hz), 7.13 (1H, s), 7.03 (3H, m), 6.68 (1H, d, J 8.9 Hz), 3.90 (6H, s), 3.83 (3H, s), 3.69 (6H, m) and 2.63 (6H, m).

EXAMPLE 17

4-(2-(N-Morpholino)pyridin-5-yl)-N-(3,4,5-trimethoxyphenyl)-2-pyrimidineamine

From Intermediate 1 (200 mg, 0.54 mmol), and morpholine (0.75 ml, 8.61 mmol) to give the title compound (160 mg) as a buff solid m.p. 157–158°. δH (CDCl₃) 9.40 (1H, s), 8.94 (1H, s), 8.42 (1H, d, J 5.1 Hz), 8.30 (1H, d, J 8.8 Hz), 7.37 (1H, d, 15.1 Hz), 7.26 (2H, s), 6.95 (1H, d, J 8:8 Hz), 3.77 (6H, s), 3.70–3.67 (4H, m), 3.61 (3H, s) and 3.58–2.54 (4H, m).

EXAMPLE 18

4-(2-(N-Thiomorpholino)pyridin-5-yl)-N-(3,4,5-trimethoxyphenyl)-2-pyrimidineamine From Intermediate 1 (350 mg, 0.95 mmol) and thiomorpholine (413 mg, 4 mmol) to give the title compound (353 mg) as a buff solid m.p. 177–178°. δH (CDCl₃) 8.87 (1H, d, J 2.2 Hz), 8.38 (1H, d, J 5.3 Hz), 8.20 (1H, dd, J 9.0, 2.3 Hz), 7.21 (1H, s), 7.05–7.01 (3H, m), 6.67 (1H, d, J 9.0 Hz), 4.08–4.04 (4H, m), 3.90 (6H, s), 3.84 (3H, s) and 2.71–2.67 (4H, m).

EXAMPLE 19

4-(2-(Piperid-1-yl)pyridin-5-yl)-N-(3,4,5-trimethoxyphenyl)-2-pyrimidineamine

From Intermediate 1 (700 mg, 1.89 mmol) and piperidine (0.93 ml, 9.45 mmol) to give the title compound (213 mg) as a buff solid m.p. 150°. δH (CDCl₃) 8.86 (1H, d, J 2.5 Hz), 8.35 (1H, d, J 5.3 Hz), 8.18 (1H, dd, J 9.1, 2.5 Hz), 7.14 (1H, brs), 7.03 (1H, d, J 5.3 Hz), 7.01 (2H, s), 6.67 (1H, d, J 9.1 Hz), 3.90 (6H, s), 3.84 (3H, s), 3.67–3.66 (4H, m) and 1.68 (6H,m).

EXAMPLE 20

4-(2-(2-Hydroxymethylpiperid-1-yl)pyridin-5-yl)-N-(3,4,5-trimethoxyphenyl)-2-pyrimidineamine From Intermediate 1 (300 mg, 0.8 mmol) and 2-(hydroxymethyl)piperidine (2.0 g, 17.4 mmol) to give the title compound (43 mg) as a yellow solid m.p. 93°. δH (CDCl₃) 8.78 (1H, d, J 2.0 Hz), 8.34 (1H, d, J 5.3 Hz), 8.14 (1H, dd, J 9.1, 2.3 Hz), 7.54 (1H, s), 7.00 (2H, s), 6.98 (1H, d, J 5.4 Hz), 6.71 (1H, d, J 9.1 Hz), 4.78 (1H, m), 4.04 (2H, m), 3.87 (6H, s), 3.83 (3H, s), 3.74 (2H, m), 3.17 (1H, m) and 1.71 (6H, m).

EXAMPLE 21

4-(2-(3-Hydroxymethylpiperid-1-yl)pyridin5-yl)-N-(3,4,5-trimethoxyphenyl)-2-pyrimidineamine From Intermediate 1 (750 mg, 2.02 mmol) and 3-(hydroxymethyl)piperidine (9.22 mg, 8.0 mmol) to give the title compound (825 mg) as a pale yellow solid m.p. 183–184°. δH (CDCl₃) 8.83 (1H, d, J 2.3 Hz), 8.35 (1H, d, J 5.3 Hz), 8.17 (1H, dd, J 9.0, 2.4 Hz), 7.20 (1H, s), 7.02 (3H, m), 6.70 (1H, d, J 9.0 Hz), 3.90 (6H, s), 3.87–3.80 (2H, m), 3.84 (3H, s), 3.79–3.64 (1H, m), 3.55–3.41 (3H, m), 2.98 (1H, br s), 1.91–1.84 (1H, m), 1.73–1.69 (2H,m) and 1.60–1.46 (2H,m).

EXAMPLE 22

4-(2-(4-Hydroxypiperid-1-yl)pyridin-5-yl)-N-(3,4,5-trimethoxyphenyl)-2-pyrimidineamine From Intermediate 1 (500 mg, 1.35 mmol) and 4-hydroxypiperidine (556 mg, 5.5 mmol) to give the title compound (507 mg) as a yellow solid m.p. 127–128°. δH (CDCl₃) 8.86 (1H, d, J 2.3 Hz), 8.36 (1H, d, J 5.3 Hz), 8.19 (1H, dd, J 9.0, 3.4 Hz), 7.29 (1H, s), 7.04–7.00 (3H, m), 6.69 (1H, d, J 9.0 Hz), 4.18–4.13 (2H, m), 3.98–3.88 (1H, m), 3.89 (6H, s), 3.83 (3H, s), 3.34–3.27 (2H, m), 2.05–1.95 (2H, m), 1.76 (1H, br s) and 1.61–1.52 (2H, m).

EXAMPLE 23

4-(2-(3-(R)-Dimethylaminopyrrolidin-1-yl)pyridin-5-yl)-N-(3,4,5-trimethoxyphenyl)-2-pyrimidineamine From Intermediate 1 (350 mg, 0.95 mmol) and 3(R)-dimethylaminopyrrolidine (540 mg, 4.73 mmol) to give the title compound (220 mg) as a yellow solid m.p. 150–151°. δH (CDCl₃) 8.86 (1H, d, J 2.0 Hz), 8.35 (1H, d, J 5.3 Hz), 8.21 (1H, dd, J 8.8, 2.3 Hz), 7.17 (1H, s), 7.04–7.00 (3H, m), 6.41 (1H, d, J 8.8 Hz), 3.89 (6H, s), 3.83 (3H, s), 3.74 (1H, t, J 8.0 Hz), 3.65–3.47 (1H, m), 3.43–3.30 (1H, m), 2.89–2.83 (1H, m), 2.34 (6H, s), 2.29–2.25 (1H, m) and 2.04–1.93 (2H, m).

EXAMPLE 24

4-(2-(3(S)-Dimethylaminopyrrolidin-1-yl)pyridin-5-yl)-N-(3,4,5-trimethoxyphenyl)-2-pyrimidineamine From Intermediate 1 (350 mg, 0.95 mmol) and (S)-3-dimethylaminopyrrolidine (540 mg, 4.73 mmol) to give the title compound as a yellow solid m.p. 149–150°. δH (CDCl₃) 8.86 (1H, d, J 2.0 Hz), 8.35 (1H, d, J 5.3 Hz), 8.21 (1H, dd, J 8.8, 2.3 Hz), 7.17 (1H, s), 7.04–7.00 (3H, m), 6.41 (1H, d, J 8.8 Hz), 3.89 (6H, s), 3.83 (3H, s), 3.74 (1H, t, J 8.0 Hz), 3.65–3.47 (1H, m), 3.43–3.30 (1H, m), 2.89–2.83 (1H, m), 2.34 (6H, s), 2.29–2.25 (1H, m) and 2.04–1.93 (2H, m).

EXAMPLE 25

4-(2-(3-Hydroxyazetidin-1-yl)pyridin-5-yl)-N-(3,4,5-trimethoxyphenyl)-2-pyrimidineamine From Intermediate 1 (370 mg, 1.0 mmol) and 3-hydroxyazetidine (350 mg, 3.2 mmol) to give the title compound (115 mg) as a yellow solid m.p. 186–187°. δH (CDCl₃) 8.81 (1H, d, J 2.3 Hz), 8.36 (1H, d, J 5.3 Hz), 8.16 (1H, dd, J 8.7, 2.3 Hz), 7.34 (1H, br s), 7.00 (1H, d, J 5.3 Hz), 6.97 (2H, s), 6.29 (1H, d, J 8.7 Hz), 4.85–4.80 (1H, m), 4.40–4.35 (2H, m), 3.98–3.93 (2H, m), 3.88 (6H, s) and 3.83 (3H, s).

EXAMPLE 26

4-(2-(4-Methyl-1,4-diazacycloheptan-1-yl)pyridin-5-yl)-N-(3,4,5-trimethoxyphenyl)-2-pyrimidineamine From Intermediate 1 (500 mg, 1.34 mmol) and 1-methylhomopiperazine (1.67 ml, 13.4 mmol) to give the title compound (92 mg) as a buff solid m.p. 141°. δH (CDCl₃) 8.86 (1H, d, J 2.1 Hz), 8.35 (1H, d, J 5.3 Hz), 8.19 (1H, dd, J 9.1, 2.4 Hz), 7.09 (1H, br s), 7.03 (1H, d, J 5.3 Hz), 7.02 (2H, s), 6.54 (1H, d, J 9.1 Hz), 3.91 (8H, br s), 3.84 (3H, s), 3.72 (2H, t, J 6.2 Hz), 2.74 (2H, t, J 4.9 Hz), 2.60 (2H, t, J 5.3 Hz), 2.39 (3H, s) and 2.04 (2H, m).

EXAMPLE 27

4-(2-(3(S),4-Dimethylpiperazin-1-yl)pyridin-5-yl)-N-(3,4,5-trimethoxyphenyl)-2-pyrimidineamine To a suspension of potassium carbonate (70 mg, 0.5 mmol) in dry tetrahydrofuran (15 ml) under a nitrogen atmosphere was added the compound of Example 5 (180 mg, 0.41 mmol) followed by iodomethane (0.028 ml, 0.45 mmol) and the mixture stirred at room temperature for 2 h. After this time the solvent was removed under reduced pressure and the residue subjected to column chromatography [SiO₂; 7% methanol-dichloromethane] to give the title comopund (120 mg) as a pale yellow solid m.p. 92–93°. δH (CDCl₃) 8.87 (1H, d, J 2.4 Hz), 8.36 (1H, d, J 5.3 Hz), 8.21 (1H, dd, J 9.0, 2.5 Hz), 7.14 (1H, s), 7.03 (1H, d, J 5.3 Hz), 7.01 (2H, s), 6.68 (1H, d, J 9.0 Hz), 4.24–4.17 (2H, m), 3.90 (6H, s), 3.84 (3H, s), 3.21–3.12 (1H, m), 2.93–2.88 (1H, m), 2.76 (1H, dd, J 13.1, 10.2 Hz), 2.34 (3H, s), 2.33–2.29 (1H, m), 2.20–2.10 (1H, m) and 1.17 (3H, d, J 6.2 Hz). The following compound was prepared in a similar manner:

EXAMPLE 28

4-(2-(3(R),4-Dimethylpiperazin-1-yl)pyridin-5-yl)-N-(3,4,5-trimethoxyphenyl)-2-pyrimidineamine From the compound of Example 6 (180 mg, 0.41 mmol), iodomethane (0.028 ml, 0.45 mmol) and potassium carbonate (70 mg, 0.5 mmol) to give the title compound (150 mg) as a pale yellow solid m.p. 92–93°. δH (CDCl₃) 8.87 (1h, d, J 2.4 Hz), 8.36 (1H, d, J 5.3 Hz), 8.21 (1H, dd, J 9.0, 2.5 Hz), 7.14 (1H, s), 7.03 (1H, d, J 5.3 Hz), 7.01 (2H, s), 6.68 (1H, d, J 9.0 Hz), 4.24–4.17 (2H, m), 3.90 (6H, s), 3.84 (3H, s), 3.21–3.12 (1H, m), 2.93–2.88 (1H, m), 2.76 (1H, dd, J 13.1, 10.2 Hz), 2.34 (3H, s), 2.33–2.29 (1H, m), 2.20–2.10 (1H, m), and 1.17 (3H, d, J 6.2 Hz).

EXAMPLE 29

4-(2-(4-(3-Phthalimidopropyl)piperazin-1-yl)pyridin-5-yl)-N-(3,4,5-trimethoxyphenyl)-2-pyrimidineamine To a suspension of caesium carbonate (245 mg, 0.75 mmol) in DMF (20ml) was added the compound of Example 1 (300 mg, 0.71 mmol) and 3-bromopropylphthalimide (191 mg, 0.71 mmol) and the mixture stirred at room temperature for 4 h. The solvent was removed under reduced pressure and the residue subjected to column chromatography [silica; 1% methanol-dichloromethane] to give the title compound (180 mg) as a pale yellow solid m.p. 105–106°. δH (CDCl₃) 8.86 (1H, d, J 2.3 Hz), 8.37 (1H, d, J 5.3 Hz), 8.19 (1H, dd, J 9.0, 2.3 Hz), 7.88–7.82 (2H, m), 7.72–7.68 (2H, m), 7.17

(1H, br s), 7.03–7.00 (3H, m), 6.64 (1H, d, J 9.0 Hz), 3.90 (6H, s), 3.84 (3H, s), 3.86–3.80 (2H, m), 3.58–3.48 (4H, m), 2.53–2.42 (6H, m) and 1.95–1.89 (2H, m).

EXAMPLE 30

4-(2-(4-N,N-Dimethylsulphamoyl)piperazin-1-yl)pyridin-5-yl)-N-(3,4,5-trimethoxyphenyl)-2-pyrimidineamine To a solution of the compound of Example 1 (300 mg, 0.71 mmol) and triethylamine (0.11 ml, 0.8 mmol) at room temperature was added dimethylsulphamoyl chloride (115 mg, 0.8 mmol) and the mixture stirred for 3 h. The solvent was removed in vacuo and the residue subjected to column chromatography [silica 4% methanol-dichloromethane] to give the title compound (381 mg) as a pale yellow solid m.p. 215–216°. $\delta H$ (CDCl$_3$) 8.88 (1H, d, J 2.3 Hz), 8.39 (1H, d, J 5.3 Hz), 8.23 (1 H, dd, J 9.0, 2.3 Hz), 7.23 (1H, br s), 7.04 (1H, d, J 5.3 Hz), 7.01 (2H, s), 6.70 (1H, d, J 9.0 Hz), 3.89 (6H, s), 3.84 (3H, s), 3.77–3.73 (4H, m), 3.38–3.35 (4H, m) and 2.87 (6H, s).

The following compounds of Examples 31–33 were prepared in a manner similar to the compound of Example 1.

EXAMPLE 31

N-(4-(2-N,N-Dimethylaminoethoxy)phenyl)-4-(2-(piperazin-1-yl)pyridin-5-yl)-2-pyrimidineamine From 4-(2-chloropyridin-5-yl)-N-(4-(2-N'N'-dimethylaminoethoxy)phenyl)-2-pyrimidineamine (410 mg, 1.11 mmol) and piperazine (286 mg, 3.3 mmol) to give the title compound (210 mg) as a pale yellow solid m.p. 161–166°. $\delta H$ (CDCl$_3$) 8.87 (1H, d, J 2.4 Hz), 8.33 (1H, d, J 5.3 Hz), 8.15 (1H, dd, J 9.0, 2.4 Hz), 7.54 (2H, m), 7.18 (1H, s), 6.98 (1H, d, J 5.3 Hz), 6.93 (2H, m), 6.68 (1H, d, J 9.0 Hz), 4.07 (2H, t, J 5.7 Hz), 3.64 (4H, m), 2.99 (4H, m), 2.74 (2H, t, J 5.7 Hz) and 2.35 (6H, s).

The pyrimidineamine used as starting material was prepared in a manner similar to the analogous starting material in Example 1, from Intermediate 2 (0.79 g, 3.7 mmol), 4-(2-N',N'-dimethylaminoethoxy)phenylguanidine dinitrate (1.3 g, 3.7 mmol) and powdered sodium hydroxide (0.33 g, 8.2 mmol) to give the desired product (440 mg) as a yellow solid, which was used without purification. $\delta H$ (DMSO) 9.56 (1H, s), 9.13 (1H, br s), 8.53 (2H, m), 7.66 (3H, m), 7.41 (1H, d, J 4.7 Hz), 6.90 (2H, d, J 8.4 Hz), 4.01 (2H, m), 2.62 (2H, m) and 2.20 (6H, s).

The guanidine was prepared by heating a solution of 4-(2-dimethylaminoethoxy)aniline (1.9 g, 10.6 mmol) and cyanamide (1.06 g, 24.7 mmol) in ethanol (5 ml) at reflux, in the presence of concentrated nitric acid (1.4 ml). After heating for 13 h the solvent was removed under reduced pressure and the residue triturated with ethyl acetate and methanol to give the desired product (1.7 g) as a grey solid m.p. 149–152°. $\delta H$ (d$^6$ DMSO) 9.60 (0.6H, br s), 9.41 (1H, s), 7.20 (6H, m), 7.05 (2H, d, J 8.8 Hz), 4.30 (2H, m), 3.50 (2H, m), 2.86 (6H, s).

EXAMPLE 32

N-(3,5-Dimethoxyphenyl)-4-(2-(piperazin-1-yl)pyridin-5-yl)-2-pyrimidineamine

From 4-(2-chloropyridin-5-yl)-N-(3,5-dimethoxyphenyl)-2-pyrimidineamine (500 mg, 1.46 mmol) and piperazine (376 mg, 4.4 mmol) to give the title compound (380 mg) as a white solid. $\delta H$ (d$^6$ DMSO) 9.47 (1H, s), 8.91 (1H, d, J 2.4 Hz), 8.42 (1H, d, J 5.3 Hz), 8.24 (1H, dd, J 9.0, 2.4 Hz), 7.29 (1H, d, J 2.4 Hz), 7.13 (2H, m), 6.92 (1H, d, J 9.0 Hz), 6.12 (1H, t, J 2.2 Hz), 3.73 (6H, s), 3.55 (4H, m), 3.26 (1 H, br s) and 2.78 (4H, m).

The pyrimidineamine used as starting material was prepared from Intermediate 2 (0.81 g, 3.87 mmol), 3,5-dimethoxyphenylguanidine nitrate (1.0 g, 3.87 mmol) and powdered sodium hydroxide (0.17g, 4.26 mmol) to give the desired product (690 mg) as a pale yellow solid m.p. 176–177°. $\delta H$ (d$^6$ DMSO) 9.72 (1H, s), 9.16 (1H, d, J 2.1 Hz), 8.62 (1H, d, J 5.1 Hz), 8.54 (1H, dd, J 8.4, 2.5 Hz), 7.72 (1H, d, J 8.4 Hz), 7.51 (1H, d, J 5.1 Hz), 7.12 (2H, m), 6.15 (1H, t, J 2.3 Hz) and 3.73 (6H, s).

The guanidine starting material was prepared from 3,5-dimethoxyaniline (2 g, 13.0 mmol) and cyanamide as described in Example 31 to give the desired product (2.3 g) as a grey solid m.p. 181–183°. $\delta H$ (d$^6$ DMSO) 9.56 (1H, s), 7.36 (4H, s), 6.41 (1H, d, J 2.0 Hz), 6.38 (2H, d, J 2.0 Hz) and 3.74 (6H, s).

EXAMPLE 33

N-(3,4-Dimethoxyphenyl)-4-(2-piperazin-1-yl)pyridin-5-yl-2-pyrimidineamine

From 4-(2-chloropyridin-5-yl)-N-(3,4-dimethoxyphenyl)-2-pyrimidineamine (300 mg, 0.87 mmol) and piperazine (150 mg, 1.75 mmol) to give the title compound (203 mg) as a beige solid m.p. 185–188°. $\delta H$ (d$^6$ DMSO) 9.30 (1H, s), 8.90 (1H, d, J 2.3 Hz), 8.38 (1H, d, J 5.3 Hz), 8.23 (1H, dd, J 9.1, 2.6 Hz), 7.55 (1H, d, J 2.3 Hz), 7.28 (1H, dd, J 8.7, 2.4 Hz), 7.23 (1H, d, J 5.3 Hz), 6.89 (2H, m), 3.76 (3H, s), 3.71 (3H, s), 3.59 (4H, m) and 2.77 (4H, m).

The pyrimidineamine used as starting material was prepared from Intermediate 2 (0.81 g, 3.87 mmol), 3,4-dimethoxyphenylguanidine nitrate (1.0 g, 3.87 mmol) and powdered sodium hydroxide (0.17, 4.26 mmol) to give the desired product (650 mg) as a yellow solid. $\delta H$ (CDCl$_3$) 9.05 (1H, d, J 1.8 Hz), 8.49 (1H, d, J 5.2 Hz), 8.31 (1H, dd, J 8.3, 2.4 Hz), 7.44 (1H, d, J 8.3 Hz), 7.38 (1H, d, J 2.5 Hz), 7.15 (1H, s), 7.08 (2H, m), 6.88 (1H, d, J 8.6 Hz), 3.92 (3H, s) and 3.89 (3H, s).

The guanidine used as starting material was prepared from 4-aminoveratrole (3 g, 19.6 mmol) and cyanamide (1.2 g, 29.4 mmol) as described in Example 31 to give the desired product (3.73 g) as a buff solid m.p. 236–238°. $\delta H$ (d$^6$ DMSO) 9.37 (1H, br s), 7.19 (4H, br s), 6.98 (1H, d, J 8.6 Hz), 6.83 (1H, d, J 2.4 Hz), 6.76 (1H, dd, J 8.6, 2.4 Hz) and 3.75 (6H, s).

EXAMPLE 34

N-(3,5-Dimethylphenyl)-4-(2-(piperazin-1-yl)pyridin-5-yl)-2-pyrimidineamine bistrifluoroacetate A solution of 4-(2-(4-tert-butoxycarbonylpiperazin-1-yl)pyridin-5-yl)-N-(3,5-dimethylphenyl)-2-pyrimidineamine (45 mg, 98 mmol) in dichloromethane (1 ml) at 0° was treated with trifluoroacetic acid (1 $\mu$l) and stirred for 1 h. The solvent was removed under reduced pressure and the residue triturated with ether to give the title compound (59 mg) as a yellow solid m.p. 204–206°. $\delta H$ (d$^6$ DMSO) 9.42 (1H, s), 8.96 (1H, d, J 2.3 Hz), 8.85 (2H, br s), 8.45 (1H, d, J 5.2 Hz), 8.33 (1H, dd, J 9.0, 2.3 Hz), 7.44 (2H, s), 7.33 (1H, d, J 5.2 Hz), 7.08 (1H, d, J 9.0 Hz), 6.61 (1H, s), 3.85 (4H, m), 3.21 (4H, m) and 2.25 (6H, s).

The pyrimidineamine used as starting material in the above process was prepared by the following method:

A mixture of 3,5-dimethylaniline (130 mg, 1.06 mmol) and 2-chloro-4-(2-(4-tert-butoxycarbonylpiperazin-1-yl)pyridin-5-yl)pyrimidine (100 mg, 0.27 mmol) in toluene (2 ml) containing pyridine (0.1 ml) was heated at reflux for 12 h. The solvent was removed under reduced pressure and the residue subjected to column chromatography [silica; ethyl acetate-hexane] to give the desired product (46 mg) as a beige solid after recrystallisation from dichloromethane/hexane δH (CDCl$_3$) 8.86 (1H, d, J 2.3 Hz), 8.36 (1H, d, J 5.2 Hz), 8.21 (1H, dd, J 9.0, 2.4 Hz), 7.31 (3H, s), 7.01 (1H, d, J 5.2 Hz), 6.68 (2H, m), 3.66 (4H, m), 3.55 (4H, m), 2.33 (6H, s) and 1.49 (9H, s). The pyrimidine intermediate was prepared as follows:

A solution of 5-bromo-2-(4-tert-butoxycarbonylpiperazin-1-yl)pyridine (6.0 g, 17.5 mmol) in anhydrous THF (150 ml) was cooled to −100° then treated dropwise with tert-butyllithium (22.0 ml of a 1.7M solution in pentane, 37.4 mmol) and the resulting thick yellow mixture stirred at −100° for 30 min. Zinc chloride (35.2 ml of a 0.5M solution in THF, 17.60 mmol) was slowly added and the mixture stirred at −75° for 30 min then allowed to warm to room temperature whereupon 2,4-dichloropyrimidine (3.98 g, 26.71 mmol) and tetrakis(triphenylphosphine)palladium(o) (1.0 g, 0.86 mmol) were added. The resulting mixture was refluxed for 5 h then allowed to cool to room temperature. Saturated aqueous ammonium chloride was added and the mixture was extracted three times with ethyl acetate. The organic phase was washed with brine then dried (MgSO$_4$) and evaporated to give the crude product which was recrystallised from ethyl acetate/hexane to give the desired pyrimidine (3.03 g) as a beige solid m.p. 182–183°. δH (CDCl$_3$) 8.82 (1H, d, J 2.5 Hz), 8.49 (1H, d, J 5.4 Hz), 8.24 (1H, dd, J 9.0, 2.5 Hz), 7.49 (1H, d, J 5.4 Hz), 6.68 (1H, d, J 9.0 Hz), 3.69 (4H, m), 3.56 (4H, m) and 1.48 (9H, s).

The pyridine intermediate was prepared by treating a suspension of 5-bromo-2-(piperazin-1-yl)pyridine (7.0 g, 28.9 mmol) with di-tert-butyldicarbonate (6.30 g, 28.9 mmol) and the resulting mixture stirred for 2 h. The solvent was removed under reduced pressure to give the desired product (8.76 g as a beige solid after recrystallisation from aqueous ethanol, m.p. 88–90°. δH (CDCl$_3$) 8.18 (1 H, d, J 2.5 Hz), 7.52 (1H, dd, J 9.0, 2.5 Hz), 6.52 (1H, d, J 9.0 Hz), 3.50 (8H, m) and 1.47 (9H, s). The 5-bromo-2-(piperazin-1-yl)pyridine was prepared by heating a mixture of 2,5-dibromopyridine (10.0 g, 42.4 mmol) and piperazine (7.98g, 92.8 mmol) as a melt at 125° for 3 h. On cooling to room temperature the mixture was triturated with methanol-dichloromethane to afford the desired product (7.0g) as a beige solid. δH (CDCl$_3$) 8.18 (1H, d, J 2.1 Hz), 7.25 (1H, dd, J 9.1, 2.1 Hz), 6.52 (1H, d, J 9.1 Hz), 3.47 (4H, m), 2.97 (4H, m) and 1.75 (1H br s).

EXAMPLES 35–65

The compounds of Examples 35–65 were prepared by solid-phase synthesis using the following derivatised resin:
4-(5-(2-Chloropyrimidin-4-yl)(pyridin-2-yl)piperazine-1-carbonate Derivatised Resin (1)

To a solution of 2-chloro-4-(2-(4-tert-butoxycarbonylpiperazin-1-yl)pyridin-5-yl)-pyrimidine (2.81 g, 7.5 mmol) in dichloromethane (25 ml) was added trifluoroacetic acid (10 mls) and the mixture stirred for 4 hours at room temperature. The solution was evaporated to dryness in vacuo and re-evaporated from ether (25 mls) twice to yield a yellow solid containing 2-chloro-4-(2-(piperazin-1-yl)pyridin-5-yl)pyrimidine.

To a suspension of Fluka Tentagel-S-PHB Resin (10.0 g, 2.4 mmol eq.) in dichloromethane was added triethylamine (5mls), 4-nitrophenylchloroformate (2.01 g, 10 mmol) and the mixture swirled at room temperature for 17 hours. The resin was filtered under a stream of nitrogen and washed sequentially with DMF and dichloromethane. The resulting derivatised resin was dried under a stream of nitrogen for 30 minutes and suspended in DMF (40mls). Triethylamine (5 ml), 4-dimethylaminopyridine (about 100 mg) and the yellow solid prepared above were added and the mixture swirled at room temperature for 48 hours. The resin was filtered and washed thoroughly with DMF (2×50 mls) and dichloromethane (4×50 mls). The resin was suspended in methanol/water (9:1) (100 ml) containing lithium hydroxide (1%) for ten minutes. The resin was filtered and washed successively with methanol, dichloromethane/methanol (1:1) and dichloromethane and air dried on the filter funnel to give the desired derivatised resin (1).

The 2-chloro-4-(2-(4-tert-butoxycarbonylpiperazin-1-yl)pyridin-5-yl)-pyrimidine used as starting material in the above preparation was prepared as follows:

A mixture of 2,5-dibromopyridine (10.00 g, 42.21 mmol) and piperazine (7.98 g, 92.79 mmol) were heated as a melt at 125° for 3 h. On cooling to room temperature the mixture was triturated with 10% methanol-dichloromethane and filtered. The filtrate was evaporated and the residue subjected to column chromatography (silica, 5–8% methanol-dichloromethane) to afford the 5-bromo-2-(1-piperazinyl) pyridine (7.00 g) as a beige solid δ$_H$ (CDCl$_3$) 2.75 (1H, br s), 2.97 (4H, m), 3.47 (4H, m), 6.52 (1H, d, J 9.1 Hz), 7.52 (1H, dd, J 9.1, 2.1 Hz), and 8.18 (1H, d, J 2.1 Hz).

A suspension of the bromopyridine (7.00 g, 28.91 mmol) in THF (60 ml) at room temperature was treated with di-tert-butyldicarbonate (6.30 g, 28.90 mmol) and the resulting mixture stirred for 2 h, then evaporated and the crude product purified by recrystallisation (ethanol-water) to afford the 5-Bromo-2-(4-tert-butoxycarbonylpiperazin-1-yl)pyridine (8.76 g) as a beige solid m.p. 88–90°. δ$_H$ (CDCl$_3$) 1.47 (9H, s), 3.50 (8H, m), 6.52 (1H, d, J 9.0 Hz), 7.52 (1H, dd, J 9.0, 2.5 Hz) and 8.18 (1H, d, J 2.5 Hz).

A solution of the protected bromopyridine (6.00 g, 17.50 mmol) in anhydrous THF (150 ml) was cooled to −100° (liquid nitrogen-diethyl ether) then treated dropwise with tert-butyllithium (22.0 ml of a 1.7M solution in pentane, 37.40 mmol) and the resulting thick yellow mixture stirred at −100° for 30 min. Zinc chloride (35.2 ml of a 0.5M solution in THF, 17.60 mmol) was slowly added and the mixture stirred at −75° for 30 min then allowed to warm to room temperature whereupon 2,4-dichloropyrimidine (3.98 g, 26.71 mmol) and tetrakis(triphenylphosphine)-palladium (o) (1.00 g, 0.86 mmol) were added. The resulting mixture was refluxed for 5 h then allowed to cool to room temperature. Saturated aqueous ammonium chloride was added and the mixture was extracted three times with ethyl acetate. The organic phase was washed with brine then dried (MgSO$_4$) and evaporated to give a crude product which was purified by recrystallisation (ethyl acetate-hexane) to afford the desired chloropyridine (3.03 g) as a beige solid m.p. 182–183°. δ$_H$ (CDCl$_3$) 1.48 (9H, s), 3.56 (4H, m), 3.69 (4H, m), 6.68 (1H, d, J 9.0 Hz), 7.49 (1H, d, J 5.4 Hz), 8.24 (1H, dd, J 2.5, 9.0 Hz), 8.49 (1H, d, J 5.4 Hz) and 8.82 (1H, d, J 2.5 Hz).

EXAMPLE 35

4-(2-(Piperazin-1-yl)pyridin-5-yl)-N-phenyl-2-pyrimidineamine

To the derivatised resin (1), (0.1 g), prepared above, in a ptfe-fritted reaction well was added aniline (120 μl ) and mesitylene (1.0 ml). The reaction vessel was heated to 140° C. for 18 hr then cooled to room temperature. The reaction vessel was drained and the resin was washed with three portions of methanol followed by six portions of methanol/dichloromethane (1:1) and six portions of dichloromethane.

The resin was suspended in dichloromethane (0.5 ml) and trifluoroacetic acid (0.5 ml) and swirled at room temperature for 2.5 h, filtered and washed with dichloromethane (2 portions of 0.5 mls) and the filtrate evaporated in vacuo to give the title compound.
HPLC (Conditions A) Retention time 4.085 mins
HPLC-MS (conditions B) Retention time 6.38 mins, (M+H)$^+$=333

The HPLC and HPLC-MS conditions were as follows:
HPLC Conditions A

HPLC was performed on a Waters Millenium system with a Waters 996A photodiode array detector. A Zorbax RX C18 15×0.46 cm: 5 mm particle size column, running a gradient of 90% [0.1% TFA water] 10% [0.1% TFA acetonitrile] to 10% [0.1% TFA water] 90% [0.1% TFA acetonitrile], at 1.2 ml/min with a run time of 13 minutes at ambient temperature.
HPLC-MS Conditions B HPLC-MS was performed on a Hewlet Packard 1050 using a Zorbax-SB C18, 150×2.1 mm column at 60° C., running a gradient of 15% [0.1%formic acid in acetonitrile], 85% [90% water: 10% acetonitrile 0.1% formic acid] to 70% [0.1% formic acid in acetonitrile], 30% [90% water: 10% acetonitrile 0.1% formic acid] at a flow rate of 200 ml/min. MS acquired in centroid at 2 cone voltages (27 V and 60 V), on a Micromass Quattro (triple quadrupole mass spectrometer) in positive ion electrospray mode of ionisation, scanning from 120–700 amu.

The following compounds of Examples 36–65 were prepared in a similar manner to the compound of Example 35, each using the starting material shown. As in Example 35, the quantities of resin and starting material employed were maintained such that the starting material was in excess. The HPLC and HPLC-MS conditions referred to in each example are those just described.

EXAMPLE 36

4-(2-(Piperazin-1-yl)pyridin-5-yl)-N-(3,4,5-trifluorophenyl)-2-pyrimidineamine
3,4,5-trifluoroaniline gave the title compound.
HPLC (Conditions A) Retention time 5.437 mins
HPLC-MS (Conditions B) Retention time 12.94 mins, (M+H)$^+$=387

EXAMPLE 37

N-(4-Methoxyphenyl)-4-(2-(piperazin-1-yl)pyridin-5-yl)-2-pyrimidineamine
4-methoxyaniline gave the title compound
HPLC (Conditions A) Retention time 4.00 mins
HPLC-MS (Conditions B) Retention time 5.29 mins, (M+H)$^+$=363

EXAMPLE 38

N-(2,4-Dimethoxyphenyl)-4-(2-(piperazin-1-yl)pyridin-5-yl)-2-pyrimidineamine
2,4-dimethoxyaniline gave the title compound
HPLC (Conditions A) Retention time 4.072 mins
HPLC-MS (Conditions B) Retention time 6.31 mins, (M+H)$^+$=393

EXAMPLE 39

N-(4-Carboxamidophenyl)-4-(2-(piperazin-1-yl)pyridin-5-yl)-2-pyrimidineamine
4-aminobenzamide gave the title compound
HPLC (Conditions A) Retention time 3.547 mins
HPLC-MS (Conditions B) Retention time 3.53 mins, (M+H)$^+$=376

EXAMPLE 40

N-(4-Phenoxyphenyl)-4-(2-(piperazin-1-yl)pyridin-5-yl)-2-pyrimidineamine
4-phenoxyaniline gave the title compound
HPLC (Conditions A) Retention time 5.425 mins
HPLC-MS (Conditions B) Retention time 13.36 mins, (M+H)$^+$=425

EXAMPLE 41

N-(3,4-Dimethylphenyl)-4-(2-(piperazin-1-yl)pyridin-5-yl)-2-pyrimidineamine
3,4-dimethylaniline gave the title compound
HPLC (Conditions A) Retention time 4.682 mins
HPLC-MS (Conditions B) Retention time 11.59 mins, (M+H)$^+$=362

EXAMPLE 42

N-(4-Hydroxyphenyl)-4-(2-(piperazin-1-yl)pyridin-5-yl)-2-pyrimidineamine
4-hydroxyaniline gave the title compound
HPLC (Conditions A) Retention time 3.348 mins
HPLC-MS (Conditions B) Retention time 3.53 mins, (M+H)$^+$349

EXAMPLE 43

N-(3-Nitrophenyl)-4-(2-(piperazin-1-yl)pyridin-5-yl)-2-pyrimidineamine
3-nitroaniline gave the title compound
HPLC-MS (Conditions B) Retention time 11.0 mins, (M+H)$^+$=378

EXAMPLE 44

N-(4-Chlorophenyl)-4-(2-(piperazin-1-yl)pyridin-5-yl)-2-pyrimidineamine
4-chloroaniline gave the title compound
HPLC (Conditions A) Retention time 4.927 mins
HPLC-MS (Conditions B) Retention time 12.18 mins, (M+H)$^+$=367/369

EXAMPLE 45

N-(1-Naphthyl)-4-(2-(piperazin-1-yl)pyridin-5-yl)-2-pyrimidineamine
1-naphthylamine gave the title compound
HPLC (Conditions A) Retention time 4.493 mins
HPLC-MS (Conditions B) Retention time 10.83 mins, (M+H)$^+$=383

EXAMPLE 46

N-(3-Hydroxymethylphenyl)-4-(2-(piperazin-1-yl)pyridin-5-yl)-2-pyrimidineamine
3-hydroxymethylaniline gave the title compound
HPLC (Conditions A) Retention time 3.553 mins
HPLC-MS (Conditions B) Retention time 3.86 mins, (M+H)$^+$=363

EXAMPLE 47

N-(5-Indanyl)-4-(2-(piperazin-1-yl)pyridin-5-yl)-2-pyrimidine-amine
5-aminoindane gave the title compound
HPLC (Conditions A) Retention time 4.827 mins
HPLC-MS (Conditions B) Retention time 12.35 mins, (M+H)$^+$=373

EXAMPLE 48

N-(3-Carboxyphenyl)-4-(2-(piperazin-1-yl)pyridin-5-yl)-2-pyrimidineamine
3-aminobenzoic acid gave the title compound HPLC (Conditions A) Retention time 4.028 mins
HPLC-MS (Conditions B) Retention time 4.79 mins, (M+H)$^+$=377

EXAMPLE 49

N-(4-N,N-Dimethylaminophenyl)-4-(2-(piperazin-1-yl)pyridin-5-yl)-2-pyrimidineamine
4-N,N-dimethylaminoaniline gave the title compound
HPLC (Conditions A) Retention time 3.337 mins
HPLC-MS (Conditions B) Retention time 3.44 mins, (M+H)$^+$=376

EXAMPLE 50

N-(3-Chloro-4-fluorophenyl)-4-(2-(piperazin-1-yl)pyridin-5-yl)-2-pyrimidineamine
3-Chloro-4-fluoroaniline gave the title compound
HPLC (Conditions A) Retention time 5.155 mins
HPLC-MS (Conditions B) Retention time 12.52 mins, (M+H)$^+$=385/387

EXAMPLE 51

N-(Benzo[d][1,3]dioxol-5-yl)-4-(2-(piperazin-1-yl)pyridin-5-yl)-2-pyrimidineamine
benzo[d][1,3]dioxan-5-amine gave the title compound
HPLC (Conditions A) Retention time 4.040 mins
HPLC-MS (Conditions B) Retention time 5.63 mins, (M+H)$^+$=377

EXAMPLE 52

4-(2-(Piperazin-1-yl)pyridin-5-yl)-N-(3-(1,1,2,2-tetrafluoroethoxy)phenyl)-2-pyrimidineamine
3-(1,1,2,2-Tetrafluoroethoxy)aniline gave the title compound
HPLC (Conditions A) Retention time 5.473 mins
HPLC-MS (Conditions B) Retention time 13.02 mins, (M+H)$^+$=449

EXAMPLE 53

N-(3-Chlorophenyl)-4-(2-(piperazin-1-yl)pyridin-5-yl)-2-pyrimidineamine
3-chloroaniline gave the title compound
HPLC (Conditions A) Retention time 5.023 mins
HPLC-MS (Conditions B) Retention time 12.35 mins, (M+H)$^+$=367/369

EXAMPLE 54

N-(3-Bromophenyl)-4-(2-(piperazin-1-yl)pyridin-5-yl)-2-pyrimidineamine
3-bromoaniline gave the title compound
HPLC (Conditions A) Retention time 5.132 mins,
HPLC-MS (Conditions B) Retention time 12.60 mins, (M+H)$^+$=411/413

EXAMPLE 55

N-(3-Methoxyphenyl)-4-(2-(piperazin-1-yl)pyridin-5-yl)-2-pyrimidineamine
3-methoxyaniline gave the title compound
HPLC (Conditions A) Retention time 4.320 mins
HPLC-MS (Conditions B) Retention time 7.39 mins, (M+H)$^+$=363

EXAMPLE 56

N-(3-Fluorophenyl)-4-(2-(piperazin-1-yl)pyridin-5-yl)-2-pyrimidineamine
3-fluoroaniline gave the title compound
HPLC (Conditions A) Retention time 4.658 mins
HPLC-MS (Conditions B) Retention time 9.78 mins, (M+H)$^+$=351

EXAMPLE 57

N-(3-Methylphenyl)-4-(2-(piperazin-1-yl)pyridin-5-yl)-2-pyrimidineamine
3-methylaniline gave the title compound
HPLC (Conditions A) Retention time 4.428 mins,
HPLC-MS (Conditions B) Retention time 9.07 mins, (M+H)$^+$=347

EXAMPLE 58

N-(3,4-Dimethoxyphenylmethyl)-4-(2-(piperazin-1-yl)pyridin-5-yl)-2-pyrimidine-amine
3,4-dimethoxyaniline gave the title compound
HPLC (Conditions A) Retention time 3.795 mins
HPLC-MS (Conditions B) Retention time 3.74 mins, (M+H)$^+$=407

EXAMPLE 59

N-(4-Butoxyphenyl)-4-(2-(piperazin-1-yl)pyridin-5-yl)-2-pyrimidineamine
4-butoxyaniline gave the title compound
HPLC (Conditions A) Retention time 5.302 mins
HPLC-MS (Conditions B) Retention time 13.10 mins, (M+H)$^+$=405

EXAMPLE 60

N-(4-Fluorophenyl)-4-(2-(piperazin-1-yl)pyridin-5-yl)-2-pyrimidineamine
4-fluoroaniline gave the title compound
HPLC (Conditions A) Retention time 4.275 mins
HPLC-MS (Conditions B) Retention time 7.22 mins, (M+H)$^+$=351

EXAMPLE 61

N-(4-Ethylphenyl)-4-(2-(piperazin-1-yl)pyridin-5-yl)-2-pyrimidineamine
4-ethylaniline gave the title compound
HPLC (Conditions A) Retention time 4.828 mins
HPLC-MS (Conditions B) Retention time 12.14 mins, (M+H)$^+$=361

EXAMPLE 62

4-(2-(Piperazin-1-yl)pyridin-5-yl)-N-(4-trifluoromethoxyphenyl)-2-pyrimidineamine
4-trifluormethoxyanilne gave the title compound
HPLC (Conditions A) Retention time 5.413 mins
HPLC-MS (Conditions B) Retention time 13.27 mins, (M+H)$^+$=417

EXAMPLE 63

4-(2-(Piperazin-1-yl)pyridin-5-yl)-N-(3-trifluoromethoxyphenyl)-2-pyrimidineamine
3-trifluoromethoxyaniline gave the title compound
HPLC (Conditions A) Retention time 5.490 mins
HPLC-MS (Conditions B) Retention time 13.27 mins, (M+H)$^+$=417

EXAMPLE 64

N-(4-N,N-Diethylaminophenyl)-4-(2-(piperazin-1-yl)pyridin-5-yl)-2-pyrimidineamine 4-N,Ndiethylaminoaniline gave the title compound
HPLC (Conditions A) Retention time 3.615 mins
HPLC-MS (Conditions B) Retention time 3.53 mins, $(M+H)^+=404$

EXAMPLE 65

N-(2,3-Dimethoxyphenyl)-4-(2-(piperazin-1-yl)pyridin-5-yl)-2-pyrimidineamine 2,3-dimethoxyaniline gave the title compound
HPLC (Conditions A) Retention time 4.322 mins
HPLC-MS (Conditions B) Retention time 9.03 mins, $(M+H)^+=393$

EXAMPLE 66

4-(2-(3(S)-Ethylpiperazin-1-yl)pyridin-5-yl)-N-(3,4,5-trimethoxyphenyl)-2-pyrimidineamine From Intermediate 1 (555 mg,1.5 mmol) and 2(S)-ethylpiperazine (500 mg, 4.38 mg) to give the title compound (445 mg) as a yellow solid m.p. 82–83°. $\delta H$ (CDCl$_3$) 8.87(1H, d, J 8.7 Hz), 8.20 (1H, dd, J 9.0, 2.5 Hz), 7.31 (1H, s), 7.03 (1H, d, J 5.3 Hz), 7.01 (2H, s), 6.66 (1H, d, J 8.6 Hz), 4.34–4.22 (2H, m), 3.88 (6H, s), 3.83 (3H, s), 3.16–3.11(1H, m), 3.03–2.86 (2H, m), 2.68–2.56 (2H, m), 1.79 (1H, br s), 1.57–1.42 (2H, m) and 1.01 (3H, t, J 7.5 Hz).

(S)-2-Ethylpiperazine was prepared by treating a suspension of (S)-3-ethylpiperazine-2,5-dione (4.5 g,31.7 mmol) in dry THF (175 ml) with LiAlH$_4$ (3.61 g, 95 mmol) in a portionwise manner at 0°. The reaction was then heated at reflux for 18 h and on cooling a 2M sodium hydroxide solution was added until a precipitate appeared. The reaction was filtered, the precipitate washed with hot ethyl acetate and the combined filtrate and washings concentrated under reduced pressure. The resulting white solid was sublimed under vacuum to give the desired product (1.1 g) as a white solid, m.p. 66–67°.

(S)-3-Ethylpiperazine-2,5-dione was prepared by adding a solution of (S)-4-ethyloxazolidine-2,5-dione (6.0 g, 46.5 mmol) in THF (75 ml) to a mixture of glycine methyl ester hydrochloride (6.13 g) and triethylamine (15.3 ml, 109.8 mmol) in chloroform at −60°. The reaction was allowed to warm to room temperature over 2.5 h. The reaction was filtered and the filtrate concentrated under reduced pressure, re-dissolved in toluene (100 ml) and heated at reflux for 15 h. The reaction was cooled in an ice-bath and the resulting precipitate collected and subjected to column chromatography to give the desired product (4.7 g) as a white solid, m.p. 170–171°.

EXAMPLE 67

4-(2-(5-Methyl-1,4-diazacycloheptan-1-yl)pyridin-5-yl)-N-(3,4,5-trimethoxyphenyl)-2-pyrimidineamine From Intermediate 1 (200 mg,0.54 mmol) and 5-methyl-1,4-diazacycloheptane (500 mg,4.38 mmol) to give the title compound (160 mg) as a pale yellow solid, m.p. 104–106°. $\delta H$(CDCl$_3$) 8.87 (1H, d, J 2.3 Hz), 8.36 (1H, d, J 5.3 Hz), 8.18 (1H, dd, J 9.0,2.3 Hz), 7.20 (1H, s), 7.03 (1H, d,J 5.3 Hz), 7.01 (2H, s), 6.54 (1H, d, J 9.0 Hz), 4.17–4.08 (1H, m), 3.90–3.85 (1H, m), 3.89 (6H, s), 3.84 (3H, s), 3.72–3.60 (2H, m), 3.34–3.28 (1H, m), 3.11–3.02 (1H, m), 2.96–2.88 (1H, m), 2.17–2.06 (1H, m) and 1.82–1.73 (1H, m).

5-Methyl-1,4-diazacycloheptane was prepared by hydrogenation of a solution of 1,4-dibenzyl-5-methyldiazacycloheptane in ethanol (40 ml) over 10% palladium on carbon at 20 psi and 55° for 18 h. The catalyst was removed by filtration and the filtrate concentrated under reduced pressure to give the desired product (0.5 g) as a colourless gum. $\delta H$ (CDCl$_3$) 2.90–2.60(9H, m), 1.73–1.65 (1H, m), 1.32–1.22 (1H, m) and 0.97 (3H, d, J 8.0 Hz).

EXAMPLE 68

N-(3,4,5-Trichlorophenyl)-4-(2-(piperazin-1-yl)pyridin-5-yl)-2-pyrimidineamine

A solution of 4-(2-(4-allyloxycarbonylpiperazin-1-yl)pyridin-5-yl)-N-(3,4,5-trichlorophenyl)-2-pyrimidineamine (170 mg,0.33 mmol) in dichloromethane and DMF (3 ml,1:1 mixture) was stirred with acetic acid (1 ml), dichlorobis(triphenylphosphine)palladium (II) (15 mg) and tri-n-butyltin hydride at room temperature for 5 min. The reaction was added to a saturated aqueous NaHCO$_3$ solution, which was extracted with ethyl acetate. The organic phase was dried (MgSO$_4$) and concentrated under reduced pressure. The residue was triturated with hexane and then subjected to column chromatography (silica gel with 1% ammonium hydroxide-8% methanol-dichloromethane) to give the title compound (60 mg) as an off-white solid m.p. 208–211°. $\delta H$(d6 DMSO) 10.03(1H, s), 8.91 (1H, d, J 2.5 Hz), 8.51 (1H, d, J 5.4 Hz), 8.22 (1H, dd , J 9.1, 2.5 Hz),8.16 (2H, s), 7.43 (1H, d, J 5.4 Hz), 3.56 (4H, m) and 2.78 (4H, m).

The pyrimidine starting material used in the above process was prepared by heating 4-(2-(allyloxycarbonylpiperazin-1-yl)pyridin-5-yl)-2-chloropyrimidine (0.3 g,8.3 mmol) and 3,4,5-trichloroaniline (245 mg, 8.3 mmol in ethoxyethanol (2 ml) at reflux for 24 h. On cooling the resulting precipitate was collected and recrystallised from aqueous ethanol to give the desired product (77 mg) as a beige solid, m.p.225–227°.

The chloropyrimidine was prepared by treating 2-chloro-4-(2-(4-tertbutoxycarbonylpiperazin-1-yl)pyridin-5-yl)pyrimidine in dichloromethane (15 ml) with trifluoroacetic acid (15 ml), at room temperature for 2 h. The reaction was concentrated under reduced pressure and the resulting residue suspended in dichloromethane (40 ml) and saturated sodium hydrogen carbonate (40 ml). To this was added allyl chloroformate (706 mg,5.86 mmol) and the reaction stirred at room temperature for 4 h. The organic phase was evaporated and the residue recrystallised from hexane/ethyl acetate to give the desired material (1.72 g) as a pale yellow solid, m.p. 136–138°.

BIOLOGICAL ACTIVITY

The following assays were used to demonstrate the activity and selectivity of compounds according to the invention. In each assay an IC$_{50}$ value for each test compound was determined. In each instance the IC$_{50}$ value was defined as the concentration of test compound required to inhibit 50% of the enzyme activity.

p56$^{lck}$ kinase assay

The tyrosine kinase activity of p56$^{lck}$ was determined using a RR-src peptide (RRLIEDNEYTARG) and [γ-$^{33}$P] ATP as substrates. Quantitation of the $^{33}$P-phosphorylated peptide formed by the action of p56$^{lck}$ was achieved using an adaption of the method of Geissler et al (J. Biol. Chem. (1990) 265, 22255–22261).

All assays were performed in 20 mM HEPES pH 7.5 containing 10 mM MgCl$_2$, 10 mM MnCl$_2$, 0.05% Brij, 1 μM ATP (0.5 μ Ci[γ-$^{33}$P]ATP) and 0.8 mg/ml RR-src. Inhibitors in dimethylsulphoxide (DMSO) were added such that the final concentration of DMSO did not exceed 1%, and enzyme such that the consumption of ATP was less than 10%. After incubation at 30° C. for 15 min, the reaction was terminated by the addition of one-third volume of stop reagent (0.25 mM EDTA and 33 mM ATP in dH$_2$O). A 15 μl aliquot was removed, spotted onto a P-30 filtermat (Wallac, Milton Keynes, UK), and washed sequentially with 1% acetic acid and dH$_2$O to remove ATP. The bound $^{33}$P-RR-src was quantitated by scintillation counting of the filtermat in a Betaplate scintillation counter (Wallac, Milton Keynes, UK) after addition of Meltilex scintillant (Wallac, Milton Keynes, UK). The dpm obtained, being directly proportional to the amount of $^{33}$P-RR-src produced by p56$^{lck}$, were used to determine the IC$_{50}$ for each compound.

Zap-70 kinase assay

The tyrosine kinase activity of Zap-70 was determined using a capture assay based on that employed above for p56$^{lck}$. The RR-src peptide was replaced with polyGlu-Tyr (Sigma; Poole, UK) at a final concentration of 17 μg/ml. After addition of the stopped reaction to the filtermat, trichloroacetic acid 10% (w/v) was employed as the wash reagent instead of acetic acid and a final wash in absolute ethanol was also performed before scintillation counting.

Syk and Csk kinases assays

Compounds of the invention were assayed for syk kinase and csk kinase inhibitory activity in a similar manner to the ZAP-70 assay.

EGFr kinase assay

The tyrosine kinase activity of the EGF receptor (EGFr) was determined using a similar methodology to the p56$^{lck}$ kinase assay, except that the RR-src peptide was replaced by a peptide substrate for EGFr obtained from Amersham International plc (Little Chalfont, UK) and used at the manufacturer's recommended concentration.

Protein kinase C assay

Inhibitor activity against protein kinase C (PKC) was determined using PKC obtained from Sigma Chemical Company (Poole, UK) and a commercially available assay system (Amersham International plc, Little Chalfont, UK). Briefly, PKC catalyses the transfer of the γ-phosphate ($^{32}$p) of ATP to the threonine group on a peptide specific for PKC. Phosphorylated peptide is bound to phosphocellulose paper and subsequently quantified by scintillation counting.

p34 Cdc2 kinase assay

The tyrosine kinase activity of p34cdc2 was determined using a commercially available enzyme assay (Amersham International plc, Little Chalfont, UK; product code RPNQ0170).

In the above assays, compounds according to the invention selectively inhibit ZAP-70 and syk kinases. Thus, for example, the most active compounds of the Examples each have an IC$_{50}$ value against ZAP-70 of below 500 nM. When compared with IC$_{50}$ values obtained with the other enzymes above the advantageous selectivity of the compounds becomes apparent. The most selective compounds have selectivities (as determined by the ratio of IC$_{50}$ values) in excess of 100x against p$_{56}^{lck}$, EGFr, csk, protein kinase C and p34cdc2.

We claim:

1. A compound which is selected from the group consisting of:

4-(2-(3(R)-Methylpiperazin-1-yl)pyridin-5-yl)-N-(3,4,5-trimethoxyphenyl)-2-pyrimidineamine;

4-(2-(3-(2-Hydroxyethyl)piperazin-1-yl)pyridin-5-yl)-N-(3,4,5-trimethoxyphenyl)-2-pyrimidineamine;

N-(4-(2-N,N-Dimethylaminoethoxy)phenyl)-4-(2-piperazin-1-yl)pyridin-5-yl)-2-pyrimidineamine;

4-(2-(3(S)-Ethylpiperazin-1-yl)pyridin-5-yl)-N-(3,4,5-trimethoxyphenyl)-2-pyrimidineamine;

and the salts, hydrates and N-oxides thereof.

2. A compound according to claim 1 which is 4-(2-(3(R)-Methylpiperazin-1-yl)pyridin-5-yl)-N-(3,4,5-trimethoxyphenyl)-2-pyrimidineamine; and the salts, hydrates and N-oxides thereof.

3. A compound according to claim 1 which is 4-(2-(3-(2-Hydroxyethyl)piperazin-1-yl)pyridin-5-yl)-N-(3,4,5-trimethoxyphenyl)-2-pyrimidineamine; and the salts, hydrates and N-oxides thereof.

4. A compound according to claim 1 which is N-(4-(2-N,N-Dimethylaminoethoxy)phenyl)-4-(2-piperazin-1-yl)-pyridin-5-yl)-2-pyrimidineamine; and the salts, hydrates and N-oxides thereof.

5. A compound according to claim 1 which is 4-(2-(3(S)-Ethylpiperazin-1-yl)pyridin-5-yl)-N-(3,4,5-trimethoxyphenyl)-2-pyrimidineamine; and the salts, hydrates and N-oxides thereof.

6. A pharmaceutical composition comprising, in combination with one or more pharmaceutically acceptable carriers, excipients or diluents, an effective amount of a compound according to claim 1.

* * * * *